United States Patent
Dyballa et al.

(10) Patent No.: US 9,670,108 B2
(45) Date of Patent: Jun. 6, 2017

(54) BISPHOSPHITES HAVING A CENTRAL 2,3'-BIPHENOL UNIT

(71) Applicants: Katrin Marie Dyballa, Recklinghausen (DE); Robert Franke, Marl (DE); Armin Böerner, Rostock (DE); Detlef Selent, Rostock (DE)

(72) Inventors: Katrin Marie Dyballa, Recklinghausen (DE); Robert Franke, Marl (DE); Armin Böerner, Rostock (DE); Detlef Selent, Rostock (DE)

(73) Assignee: Evonik Degussa GmbH, Essen (DE)

(*) Notice: Subject to any disclaimer, the term of this patent is extended or adjusted under 35 U.S.C. 154(b) by 18 days.

(21) Appl. No.: 14/953,152

(22) Filed: Nov. 27, 2015

(65) Prior Publication Data
US 2016/0185685 A1    Jun. 30, 2016

(30) Foreign Application Priority Data

Dec. 4, 2014 (EP) .................................... 14196179

(51) Int. Cl.
| | | |
|---|---|---|
| *C07F 15/00* | (2006.01) | |
| *C07B 41/06* | (2006.01) | |
| *B01J 31/18* | (2006.01) | |
| *C07F 9/6574* | (2006.01) | |
| *C07C 45/50* | (2006.01) | |
| *C07F 9/6571* | (2006.01) | |

(52) U.S. Cl.
CPC .............. *C07B 41/06* (2013.01); *B01J 31/185* (2013.01); *C07C 45/50* (2013.01); *C07F 9/6571* (2013.01); *C07F 9/65746* (2013.01); *C07F 15/008* (2013.01); *B01J 2231/321* (2013.01); *B01J 2531/822* (2013.01); *C07B 2200/07* (2013.01)

(58) Field of Classification Search
CPC .. C07F 15/008; C07F 9/6571; C07F 9/65746; C07C 45/50; C07B 41/06
USPC .......................... 556/13; 568/10, 13; 502/162
See application file for complete search history.

(56) References Cited

U.S. PATENT DOCUMENTS

| | | | |
|---|---|---|---|
| 4,668,651 A * | 5/1987 | Billig | B01J 31/185 502/158 |
| 9,556,096 B2 * | 1/2017 | Christiansen | C07C 45/505 |
| 2010/0036143 A1 | 2/2010 | Selent et al. | |
| 2010/0069679 A1 | 3/2010 | Puckette | |
| 2012/0190894 A1 | 7/2012 | Wegman | |

FOREIGN PATENT DOCUMENTS

| | | |
|---|---|---|
| WO | WO 2008/071508 A1 | 6/2008 |
| WO | WO 2010/030339 A1 | 3/2010 |
| WO | WO 2011/046781 A1 | 4/2011 |

OTHER PUBLICATIONS

European Search Report issued May 13, 2015 in Patent Application 14196179.7 with English translation of categories of cited documents.
Robert Franke, et al., "Applied Hydroformylation" Chemical Reviews, vol. 112, No. 11, XP055091930, Nov. 14, 2012, pp. 5675-5732.

* cited by examiner

*Primary Examiner* — Porfirio Nazario Gonzalez
(74) *Attorney, Agent, or Firm* — Oblon, McClelland, Maier & Neustadt, L.L.P.

(57) ABSTRACT

Bisphosphites having a central 2,3'-biphenol unit are useful for catalyzing hydroformylation.

19 Claims, 1 Drawing Sheet

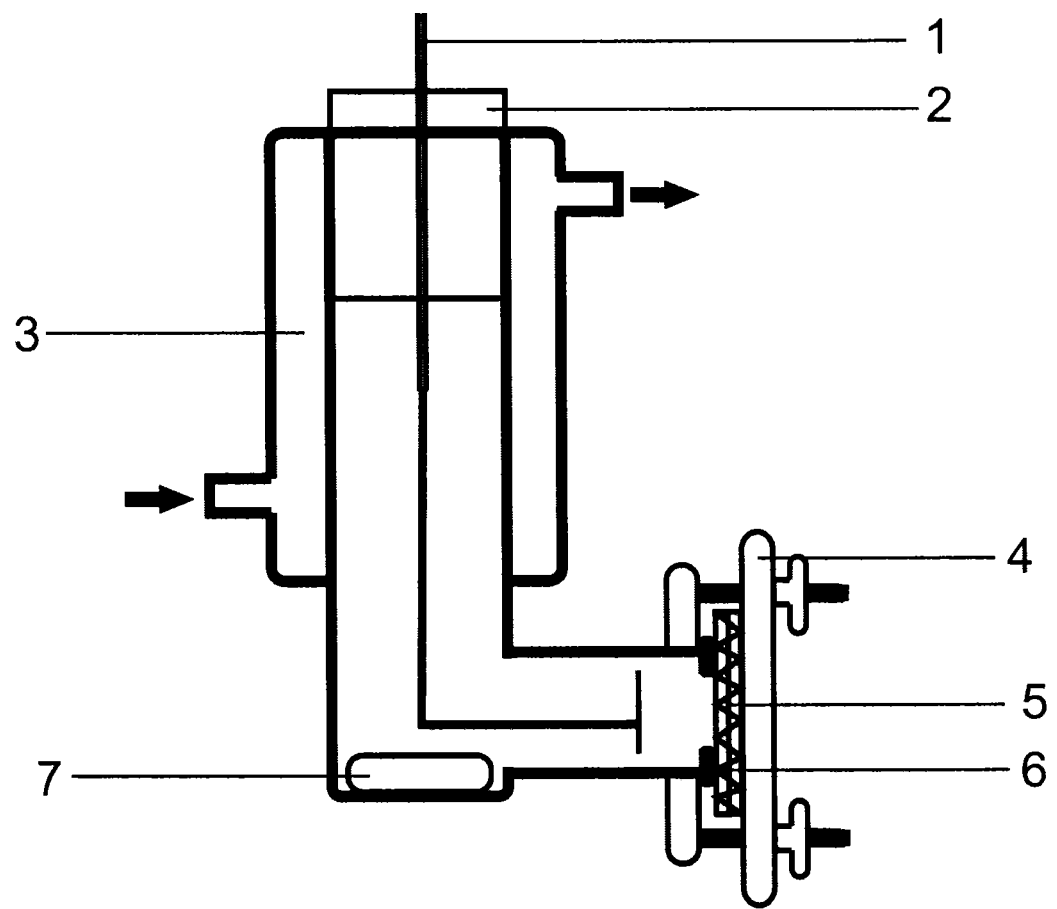

BISPHOSPHITES HAVING A CENTRAL 2,3'-BIPHENOL UNIT

BACKGROUND OF THE INVENTION

Field of the Invention

The invention relates to bisphosphites having a central 2,3'-biphenol unit. In addition, the use thereof as ligands in hydroformylation.

Discussion of the Background

A bisphosphite has a central unit, called the backbone, and two outer units bonded to the central unit via the phosphorus atom.

The compounds according to the invention have a central 2,3'-biphenol unit.

A 2,3'-biphenol unit is understood to mean a biphenol unit having the following structure:

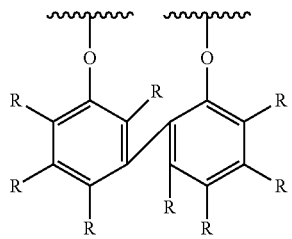

The numbering of the carbon atoms in the rings in the IUPAC name of the compound may lead to different position figures from 2 and 3 depending on additional substituents.

The reactions between olefin compounds, carbon monoxide and hydrogen in the presence of a catalyst to give the aldehydes comprising one additional carbon atom are known as hydroformylation or oxo synthesis. The catalysts used in these reactions are frequently compounds of the transition metals of group VIII of the Periodic Table of the Elements. Known ligands include, for example, compounds of the phosphine, phosphite and phosphonite classes each comprising trivalent phosphorus $P^{III}$. A good overview of the state of the hydroformylation of olefins can be found in B. CORNILS, W. A. HERRMANN, "Applied Homogeneous Catalysis with Organometallic Compounds", vol. 1 & 2, VCH, Weinheim, N.Y., 1996 or R. Franke, D. Selent, A. Börner, "Applied Hydroformylation", Chem. Rev., 2012, DOI: 10.1021/cr3001803.

Every catalytically active composition has its specific benefits. According to the feedstock and target product, therefore, different catalytically active compositions are used.

U.S. Pat. Nos. 4,694,109 and 4,879,416 describe bisphosphine ligands and use thereof in the hydroformylation of olefins at low synthesis gas pressures. Particularly in the case of hydroformylation of propene, ligands of this type achieve high activities and high n/i selectivities (n/i=the ratio of linear aldehyde (=n) to branched (=iso) aldehyde). WO 95/30680 discloses bidentate phosphine ligands and the use thereof in catalysis, including in hydroformylation reactions.

It is a feature of most of the bisphosphites known in the prior art that they have a 2,2'-biphenol as central unit, i.e. in the backbone. The use of a 2,3'-biphenol as central unit is entirely unknown.

Even though a multitude of ligands and the use thereof in rhodium-catalysed hydroformylation are known, it is desirable to develop new ligands having improved properties.

SUMMARY OF THE INVENTION

The problem addressed by the invention was that of providing bisphosphites having advantageous properties in hydroformylation compared to the known bisphosphites. The problem addressed was more particularly that of developing novel ligands which, as well as a good yield, also generate a high n selectivity for the corresponding aldehydes in the conversion of terminal olefins and which likewise have satisfactory n/i selectivities in the hydroformylation of internal olefins. As well as a very good yield, a good selectivity is thus additionally also to be achieved.

More particularly, the yield and/or the selectivity is to be enhanced.

The present invention relates to a compound of the formulae (I) or (II)

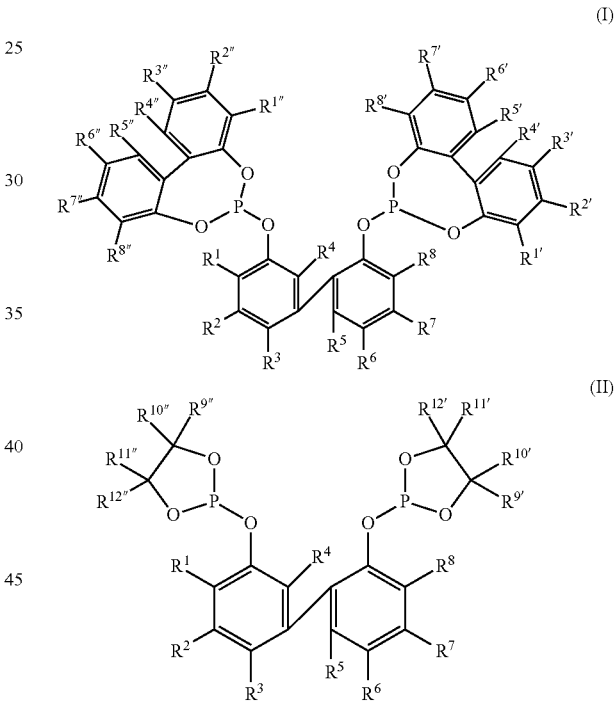

wherein $R^1$, $R^2$, $R^3$, $R^4$, $R^5$, $R^6$, $R^7$, $R^8$ are each independently selected from the group consisting of:

—H, —($C_1$-$C_{12}$)-alkyl, —O—($C_1$-$C_{12}$)-alkyl, —O—($C_6$-$C_{20}$)-aryl, —($C_6$-$C_{20}$)-aryl, —S-alkyl, —S-aryl, halogen, COO—($C_1$-$C_{12}$)-alkyl, CONH—($C_1$-$C_{12}$)-alkyl, —CO—($C_1$-$C_{12}$)-alkyl, —CO—($C_6$-$C_{20}$)-aryl, —COOH, —OH, —$SO_3H$, —CN, —$NH_2$, and —N[($C_1$-$C_{12}$)-alkyl]$_2$;

$R^{1'}$, $R^{2'}$, $R^{3'}$, $R^{4'}$, $R^{5'}$, $R^{6'}$, $R^{7'}$, $R^{8'}$, $R^{1''}$, $R^{2''}$, $R^{3''}$, $R^{4''}$, $R^{5''}$, $R^{6''}$, $R^{7''}$, $R^{8''}$ are each independently selected from the group consisting of:

—H, —($C_1$-$C_{12}$)-alkyl, —O—($C_1$-$C_{12}$)-alkyl, —O—($C_6$-$C_{20}$)-aryl, —($C_6$-$C_{20}$)-aryl, —S-alkyl, —S-aryl, halogen, COO—($C_1$-$C_{12}$)-alkyl, CONH—($C_1$-$C_{12}$)-alkyl, —CO—($C_1$-$C_{12}$)-alkyl, —CO—($C_6$-$C_{20}$)-aryl, —COOH, —OH, —$SO_3H$, —$NH_2$, and —N[($C_1$-$C_{12}$)-alkyl]$_2$;

$R^{9'}$, $R^{10'}$, $R^{11'}$, $R^{12'}$, $R^{9''}$, $R^{10''}$, $R^{11''}$, $R^{12''}$ are each independently selected from the group consisting of:

—H, and —($C_6$-$C_{20}$)-aryl;

wherein the alkyl and aryl groups may be substituted.

In one embodiment, the invention provides a complex, comprising:
a compound as above; and
a metal atom selected from the group consisting of: Rh, Ru, Co, and Ir.

The invention also relates to a catalyst for catalyzing a hydroformylation reaction, comprising: the compound as above.

The invention further relates to a process for hydroformylation of an olefin, comprising:
a) initially charging an olefin into a reactor;
b) adding
 i) a complex as above;
 or
 ii) a compound as above and a substance having a metal atom selected from the group consisting of: Rh, Ru, Co, and Ir;
c) feeding into said reactor $H_2$ and CO, to obtain a reaction mixture;
d) heating the reaction mixture, to obtain conversion of the olefin to an aldehyde.

BRIEF DESCRIPTION OF THE DRAWINGS

FIG. 1 shows a reaction apparatus in which the coupling reaction to give the corresponding unsymmetric biaryls can be conducted.

DETAILED DESCRIPTION OF THE INVENTION

The object is achieved by a compound according to the present invention which is a compound having one of the two general structures I and II:

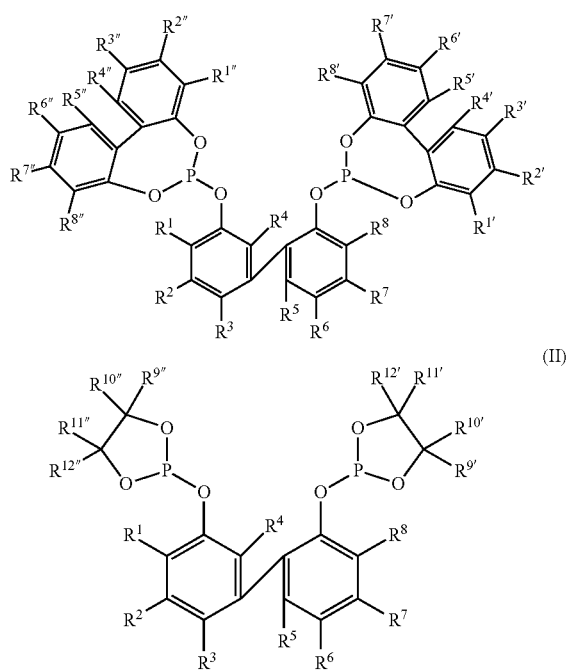

where
$R^1$, $R^2$, $R^3$, $R^4$, $R^5$, $R^6$, $R^7$, $R^8$ are selected from:
—H, —($C_1$-$C_{12}$)-alkyl, —O—($C_1$-$C_{12}$)-alkyl, —O—($C_6$-$C_{20}$)-aryl, —($C_6$-$C_{20}$)-aryl, —S-alkyl, —S-aryl, halogen, COO—($C_1$-$C_{12}$)-alkyl, CONH—($C_1$-$C_{12}$)-alkyl, —CO—($C_1$-$C_{12}$)-alkyl, —CO—($C_6$-$C_{20}$)-aryl, —COOH, —OH, —$SO_3$H, —CN, —$NH_2$, —N[($C_1$-$C_{12}$)-alkyl]$_2$;

$R^{1'}$, $R^{2'}$, $R^{3'}$, $R^{4'}$, $R^{5'}$, $R^{6'}$, $R^{7'}$, $R^{8'}$, $R^{2''}$, $R^{2''}$, $R^{3''}$, $R^{4''}$, $R^{5''}$, $R^{6''}$, $R^{7''}$, $R^{8''}$ are selected from:
—H, —($C_1$-$C_{12}$)-alkyl, —O—($C_1$-$C_{12}$)-alkyl, —O—($C_6$-$C_{20}$)-aryl, —($C_6$-$C_{20}$)-aryl, —S-alkyl, —S-aryl, halogen, COO—($C_1$-$C_{12}$)-alkyl, CONH—($C_1$-$C_{12}$)-alkyl, —CO—($C_1$-$C_{12}$)-alkyl, —CO—($C_6$-$C_{20}$)-aryl, —COOH, —OH, —$SO_3$H, —$NH_2$, —N[($C_1$-$C_{12}$)-alkyl]$_2$;

$R^{9'}$, $R^{10'}$, $R^{11'}$, $R^{12'}$, $R^{9''}$, $R^{10''}$, $R^{11''}$, $R^{12''}$ are selected from:
—H, —($C_6$-$C_{20}$)-aryl;

where the alkyl and aryl groups mentioned may be substituted.

($C_1$-$C_{12}$)-Alkyl and O—($C_1$-$C_{12}$)-alkyl may each be unsubstituted or substituted by one or more identical or different radicals selected from ($C_3$-$C_{12}$)-cycloalkyl, ($C_3$-$C_{12}$)-heterocycloalkyl, ($C_6$-$C_{20}$)-aryl, fluorine, chlorine, cyano, formyl, acyl and alkoxycarbonyl.

($C_6$-$C_{20}$)-Aryl and —($C_6$-$C_{20}$)-aryl-($C_6$-$C_{20}$)-aryl- may each be unsubstituted or substituted by one or more identical or different radicals selected from:
—H, —($C_1$-$C_{12}$)-alkyl, —O—($C_1$-$C_{12}$)-alkyl, —O—($C_6$-$C_{20}$)-aryl, —($C_6$-$C_{20}$)-aryl, -halogen (such as Cl, F, Br, I), —COO—($C_1$-$C_{12}$)-alkyl, —CONH—($C_1$-$C_{12}$)-alkyl, —($C_6$-$C_{20}$)-aryl-CON[($C_1$-$C_{12}$)-alkyl]$_2$, —CO—($C_1$-$C_{12}$)-alkyl, —CO—($C_6$-$C_{20}$)-aryl, —COOH, —OH, —$SO_3$H, —$SO_3$Na, —$NO_2$, —CN, —$NH_2$, —N[($C_1$-$C_{12}$)-alkyl]$_2$.

Any ranges herein below include all values and subvalues between the lowest and highest limits of the range.

In the context of the invention, the expression "—($C_1$-$C_{12}$)-alkyl" encompasses straight-chain and branched alkyl groups. Preferably, these groups are unsubstituted straight-chain or branched —($C_1$-$C_8$)-alkyl groups and most preferably —($C_1$-$C_6$)-alkyl groups. Examples of —($C_1$-$C_{12}$)-alkyl groups are especially methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1,1,2-trimethylpropyl, 1,2,2-trimethylpropyl, I-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

The elucidations relating to the expression "—($C_1$-$C_{12}$)-alkyl" also apply to the alkyl groups in —O—($C_1$-$C_{12}$)-alkyl, i.e. in —($C_1$-$C_{12}$)-alkoxy. Preferably, these groups are unsubstituted straight-chain or branched —($C_1$-$C_6$)-alkoxy groups.

Substituted —($C_1$-$C_{12}$)-alkyl groups and substituted —($C_1$-$C_{12}$)-alkoxy groups may have one or more substituents, depending on their chain length. The substituents are preferably each independently selected from —($C_3$-$C_{12}$)-cycloalkyl, —($C_3$-$C_{12}$)-heterocycloalkyl, —($C_6$-$C_{20}$)-aryl, fluorine, chlorine, cyano, formyl, acyl and alkoxycarbonyl.

The expression "—($C_3$-$C_{12}$)-cycloalkyl", in the context of the present invention, encompasses mono-, bi- or tricyclic hydrocarbyl radicals having 3 to 12, especially 5 to 12, carbon atoms. These include cyclopropyl, cyclobutyl, cyclopentyl, cyclohexyl, cycloheptyl, cyclooctyl, cyclododecyl, cyclopentadecyl, norbornyl and adamantyl. One example of a substituted cycloalkyl would be menthyl.

The expression "—$(C_3-C_{12})$-heterocycloalkyl groups", in the context of the present invention, encompasses nonaromatic saturated or partly unsaturated cycloaliphatic groups having 3 to 12, especially 5 to 12, carbon atoms. The —$(C_3-C_{12})$-heterocycloalkyl groups have preferably 3 to 8, more preferably 5 or 6, ring atoms. In the heterocycloalkyl groups, as opposed to the cycloalkyl groups, 1, 2, 3 or 4 of the ring carbon atoms are replaced by heteroatoms or heteroatom-containing groups. The heteroatoms or the heteroatom-containing groups are preferably selected from —O—, —S—, —N—, —N(=O)—, —C(=O)— and —S(=O)—. Examples of —$(C_3-C_{12})$-heterocycloalkyl groups are tetrahydrothiophenyl, tetrahydrofuryl, tetrahydropyranyl and dioxanyl.

In the context of the present invention, the expression "—$(C_6-C_{20})$-aryl and —$(C_6-C_{20})$-aryl-$(C_6-C_{20})$-aryl-" encompasses mono- or polycyclic aromatic hydrocarbyl radicals. These have 6 to 20 ring atoms, more preferably 6 to 14 ring atoms, especially 6 to 10 ring atoms. Aryl is preferably —$(C_6-C_{10})$-aryl and —$(C_6-C_{10})$-aryl-$(C_6-C_{10})$-aryl-. Aryl is especially phenyl, naphthyl, indenyl, fluorenyl, anthracenyl, phenanthrenyl, naphthacenyl, chrysenyl, pyrenyl, coronenyl. More particularly, aryl is phenyl, naphthyl and anthracenyl.

Substituted —$(C_6-C_{20})$-aryl groups and —$(C_6-C_{20})$-aryl-$(C_6-C_{20})$-aryl groups may have one or more (e.g. 1, 2, 3, 4 or 5) substituents, depending on the ring size. These substituents are preferably each independently selected from —H, —$(C_1-C_{12})$-alkyl, —O—$(C_1-C_{12})$-alkyl, —O—$(C_6-C_{20})$-aryl, —$(C_6-C_{20})$-aryl, -halogen (such as Cl, F, Br, I), —COO—$(C_1-C_{12})$-alkyl, —CONH—$(C_1-C_{12})$-alkyl, —$(C_6-C_{20})$-aryl-CON[$(C_1-C_{12})$-alkyl]$_2$, —CO—$(C_1-C_{12})$-alkyl, —CO—$(C_6-C_{20})$-aryl, —COOH, —OH, —SO$_3$H, —SO$_3$Na, —NO$_2$, —CN, —NH$_2$, —N[$(C_1-C_{12})$-alkyl]$_2$.

Substituted —$(C_6-C_{20})$-aryl groups and —$(C_6-C_{20})$-aryl-$(C_6-C_{20})$-aryl groups are preferably substituted —$(C_6-C_{10})$-aryl groups and —$(C_6-C_{10})$-aryl-$(C_6-C_{10})$-aryl groups, especially substituted phenyl or substituted naphthyl or substituted anthracenyl. Substituted —$(C_6-C_{20})$-aryl groups preferably bear one or more, for example 1, 2, 3, 4 or 5, substituents selected from —$(C_1-C_{12})$-alkyl groups, —$(C_1-C_{12})$-alkoxy groups.

In one embodiment, $R^1$, $R^2$, $R^3$, $R^4$, $R^5$, $R^6$, $R^7$, $R^8$ are selected from:
—H, —$(C_1-C_{12})$-alkyl, —O—$(C_1-C_{12})$-alkyl, —O—$(C_6-C_{20})$-aryl, —S-alkyl, —S-aryl.

In one embodiment, $R^1$, $R^2$, $R^3$, $R^4$, $R^5$, $R^6$, $R^7$, $R^8$ are selected from:
—H, —$(C_1-C_2)$-alkyl, —O—$(C_1-C_{12})$-alkyl, —O—$(C_6-C_{20})$-aryl.

In one embodiment, $R^4$ and $R^5$ are each —H.

In one embodiment, $R^{1'}$, $R^{2'}$, $R^{3'}$, $R^{4'}$, $R^{5'}$, $R^{6'}$, $R^{7'}$, $R^{8'}$, $R^{1''}$, $R^{2''}$, $R^{3''}$, $R^{4''}$, $R^{5''}$, $R^{6''}$, $R^{7''}$, $R^{8''}$ are selected from:
—H, —$(C_1-C_{12})$-alkyl, —O—$(C_1-C_{12})$-alkyl, —O—$(C_6-C_{20})$-aryl, —S-alkyl, —S-aryl.

In one embodiment, $R^{1'}$, $R^{2'}$, $R^{3'}$, $R^{4'}$, $R^{5'}$, $R^{6'}$, $R^{7'}$, $R^{8'}$, $R^{1''}$, $R^{2''}$, $R^{3''}$, $R^{4''}$, $R^{5''}$, $R^{6''}$, $R^{7''}$, $R^{8''}$ are selected from:
—H, —$(C_1-C_{12})$-alkyl, —O—$(C_1-C_{12})$-alkyl, —O—$(C_6-C_{20})$-aryl.

In one embodiment, $R^{1'}$, $R^{2'}$, $R^{3'}$, $R^{4'}$, $R^{5'}$, $R^{6'}$, $R^{7'}$, $R^{8'}$, $R^{1''}$, $R^{2''}$, $R^{3''}$, $R^{4''}$, $R^{5''}$, $R^{6''}$, $R^{7''}$, $R^{8''}$ are each —H.

In one embodiment, $R^{9'}$, $R^{10'}$, $R^{11'}$, $R^{12'}$, $R^{9''}$, $R^{10''}$, $R^{11''}$, $R^{12''}$ are each —$(C_6-C_{20})$-aryl.

In one embodiment, $R^{9'}$, $R^{10'}$, $R^{11'}$, $R^{12'}$, $R^{9''}$, $R^{10''}$, $R^{11''}$, $R^{12''}$ are each phenyl.

In one embodiment, $R^{9'}$, $R^{10'}$, $R^{11'}$, $R^{12'}$, $R^{9''}$, $R^{10''}$, $R^{11''}$, $R^{12''}$ are each the same radical.

In one embodiment, the compound has the general structure (I).

In one embodiment, the compound has the general structure (II).

As well as the compounds, also claimed is a complex comprising these compounds.

Complex comprising:
a compound described above,
a metal atom selected from: Rh, Ru, Co, Ir.

In a preferred embodiment, the metal is Rh.

In this regard, see R. Franke, D. Selent, A. Börner, "Applied Hydroformylation", Chem. Rev., 2012, DOI: 10.1021/cr3001803; p. 5688, Scheme 12 "General Method for the Preparation of a P-Modified Rh precatalyst" and references cited therein, and also P. W. N. M. van Leeuwen, in Rhodium Catalyzed Hydroformylation, P. W. N. M. van Leeuwen, C. Claver (eds.), Kluwer, Dordrecht, 2000, inter alia p. 48 ff., p. 233 ff. and references cited therein, and also K. D. Wiese and D. Obst in Top. Organomet. Chem. 2006, 18, 1-13; Springer Verlag Berlin Heidelberg 2006 p. 6 ff. and references cited therein.

Additionally claimed is the use of the compound as ligand in a ligand-metal complex for catalysis of a hydroformylation reaction.

Use of a compound described above in a ligand-metal complex for catalysis of a hydroformylation reaction.

The process in which the compound is used as ligand in a ligand-metal complex for conversion of an olefin to an aldehyde is likewise claimed.

A process comprising the following process steps:
a) initially charging an olefin,
b) adding an above-described complex,
or an above-described compound and a substance including a metal atom selected from: Rh, Ru, Co, Ir,
c) feeding in H$_2$ and CO,
d) heating the reaction mixture, with conversion of the olefin to an aldehyde.

In this process, process steps a) to d) can be effected in any desired sequence.

An excess of ligands can also be used in this case and each ligand is not necessarily present bound in the form of a ligand-metal complex but is present as free ligand in the reaction mixture.

The reaction is conducted under customary conditions.

Preference is given to a temperature of 80° C. to 200° C. and a pressure of 1 bar to 300 bar.

Particular preference is given to a temperature of 100° C. to 160° C. and a pressure of 15 bar to 250 bar.

The reactants for the hydroformylation in the process of the invention are olefins or mixtures of olefins, especially monoolefins having 2 to 24, preferably 3 to 16 and more preferably 3 to 12 carbon atoms, having terminal or internal C—C double bonds, for example 1-propene, 1- or 2-pentene, 2-methyl-1-butene, 2-methyl-2-butene, 3-methyl-1-butene, 1-, 2- or 3-hexene, the C$_6$ olefin mixture obtained in the dimerization of propene (dipropene), heptenes, 2- or 3-methyl-1-hexenes, octenes, 2-methylheptenes, 3-methylheptenes, 5-methyl-2-heptene, 6-methyl-2-heptene, 2-ethyl-1-hexene, the C$_8$ olefin mixture obtained in the dimerization of butenes (dibutene), nonenes, 2- or 3-methyloctenes, the C$_9$ olefin mixture obtained in the trimerization of propene (tripropene), decenes, 2-ethyl-1-octene, dodecenes, the C$_{12}$ olefin mixture obtained in the tetramerization or the trimerization of butenes (tetrapropene or tributene), tetradecenes, hexadecenes, the C$_{16}$ olefin mixture obtained in the tetramerization of butenes (tetrabutane), and olefin mixtures prepared by cooligomerization of olefins having different numbers of carbon atoms (preferably 2 to 4).

In addition, it is possible to hydroformylate mixtures of polyunsaturated hydrocarbons.

The unsaturated compounds which are hydroformylated in the process according to the invention additionally include unsaturated carboxylic acid derivatives. In particular embodiments, these unsaturated carboxylic acid derivatives are selected from fatty acid esters.

Having generally described this invention, a further understanding can be obtained by reference to certain specific examples which are provided herein for purposes of illustration only, and are not intended to be limiting unless otherwise specified.

EXAMPLES

The invention is illustrated in detail hereinafter by working examples and a FIGURE.

FIG. 1 shows a reaction apparatus in which the coupling reaction to give the corresponding unsymmetric biaryls can be conducted. The apparatus comprises a nickel cathode (1) and an anode composed of boron-doped diamond (BDD) on silicon (5). The apparatus can be cooled with the aid of a cooling jacket (3). The arrows indicate the flow direction of the cooling water. The reaction space is sealed by a Teflon stopper (2). The reaction mixture is mixed by a magnetic stirrer bar (7). On the anodic side, the apparatus is sealed by screw clamps (4) and seals (6).

Analysis

Chromatography

The preparative liquid chromatography separations via flash chromatography were conducted with a maximum pressure of 1.6 bar on 60 M silica gel (0.040-0.063 mm) from Macherey-Nagel GmbH & Co, Düren. The unpressurized separations were conducted on Geduran Si 60 silica gel (0.063-0.200 mm) from Merck KGaA, Darmstadt. The solvents used as eluents (ethyl acetate (technical grade), cyclohexane (technical grade)) had been purified by distillation beforehand on a rotary evaporator.

For thin-film chromatography (TLC), ready-made PSC silica gel 60 F254 plates from Merck KGaA, Darmstadt were used. The Rf values are reported as a function of the eluent mixture used. The TLC plates were stained using a cerium/molybdatophosphoric acid solution as immersion reagent. Cerium/molybdatophosphoric acid reagent: 5.6 g of molybdatophosphoric acid, 2.2 g of cerium(IV) sulphate tetrahydrate and 13.3 g of concentrated sulphuric acid to 200 ml of water.

Gas Chromatography (GC/GCMS)

The gas chromatography studies (GC) on product mixtures and pure substances were effected with the aid of the GC-2010 gas chromatograph from Shimadzu, Japan. Analysis is effected on an HP-5 quartz capillary column from Agilent Technologies, USA (length: 30 m; internal diameter: 0.25 mm; film thickness of the covalently bound stationary phase: 0.25 m; carrier gas: hydrogen; injector temperature: 250° C.; detector temperature: 310° C.; programme: "hard" method: start temperature 50° C. for 1 min, heating rate: 15° C./min, end temperature 290° C. for 8 min). Gas chromatography-mass spectrometry analyses (GC-MS) of product mixtures and pure substances were recorded with the aid of the GC-2010 gas chromatograph combined with the GCMS-QP2010 mass detector from Shimadzu, Japan. Analysis is effected on an HP-1 quartz capillary column from Agilent Technologies, USA (length: 30 m; internal diameter: 0.25 mm; film thickness of the covalently bound stationary phase: 0.25 µm; carrier gas: hydrogen; injector temperature: 250° C.; detector temperature: 310° C.; programme: "hard" method: start temperature 50° C. for 1 min, heating rate: 15° C./min, end temperature 290° C. for 8 min; GC-MS: ion source temperature: 200° C.).

Melting Points

Melting points were measured with the aid of the SG 2000 melting point determination instrument from HW5, Mainz, and are uncorrected.

Elemental Analysis

The elemental analyses were conducted in the analytical division of the Organic Chemistry department of the Johannes Gutenberg University of Mainz on a Vario EL Cube from Foss-Heraeus, Hanau.

Mass Spectrometry

All electrospray ionization analyses (ESI+) were conducted on a QTof Ultima 3 from Waters Micromasses, Milford, Mass. EI mass spectra and the high-resolution EI spectra were analysed on an instrument of the MAT 95 XL sector field instrument type from ThermoFinnigan, Bremen.

NMR Spectroscopy

The NMR spectroscopy studies were conducted on multinucleus resonance spectrometers of the AC 300 or AV II 400 type from Bruker, Analytische Messtechnik, Karlsruhe. The solvent used was CDCl3. The 1H and 13C spectra were calibrated according to the residual content of undeuterated solvent using the NMR Solvent Data Chart from Cambridge Isotopes Laboratories, USA. Some of the 1H and 13C signals were assigned with the aid of H,H-COSY, H,H-NOESY, H,C-HSQC and H,C-HMBC spectra. The chemical shifts are reported as δ values in ppm. For the multiplicities of the NMR signals, the following abbreviations were used: s (singlet), bs (broad singlet), d (doublet), t (triplet), q (quartet), m (multiplet), dd (doublet of doublets), dt (doublet of triplets), tq (triplet of quartets). All coupling constants J were reported in hertz (Hz) together with the number of bonds covered. The numbering given in the assignment of signals corresponds to the numbering shown in the formula schemes, which do not necessarily have to correspond to IUPAC nomenclature.

General Operating Procedures

All the preparations which follow were carried out under protective gas using standard Schlenk techniques. The solvents were dried over suitable desiccants before use (Purification of Laboratory Chemicals, W. L. F. Armarego (Author), Christina Chai (Author), Butterworth Heinemann (Elsevier), 6th edition, Oxford 2009).

Synthesis of the Chlorophosphites

6-Chlorodibenzo[df][1,3,2]dioxaphosphepin was prepared according to DE 10 2008 043 584, and 2-chloro-4,4,5,5-tetraphenyl-1,3,2-dioxaphospholane according to DE 10 2006 058 682.

Synthesis of Unsymmetric Biaryls

The unsymmetric biaryls were prepared by an electrochemical method by coupling two phenols or one naphthol and one phenol which differ in terms of oxidation potential. In this regard, see also B. Elsler, D. Schollmeyer, K. M. Dyballa, R. Franke, S. R. Waldvogel, "Metall-und reagensfreie hochselektive anodische Kreuzkupplung von Phenolen" [Metal- and Reagent-Free High-Selectivity Anodic Cross-Coupling of Phenols], Angew. Chem., 2014, DOI: 10.1002/ange.201400627

General Procedure.

The coupling reaction was conducted in an apparatus as shown in FIG. 1.

5 mmol of the first phenol having an oxidation potential $E_{Ox}1$ together with 15 mmol of the second phenol having an oxidation potential $E_{Ox}2$ are dissolved in 1,1,1,3,3,3-hexafluoroisopropanol (HFIP) and MeOH or in formic acid and MeOH in the amounts specified in Table 1 below. The electrolysis is galvanostatic.

The outer shell of the electrolysis cell is kept at a controlled temperature of about 10° C. by means of a thermostat, while the reaction mixture is stirred and heated to 50° C. with the aid of a sand bath. After the electrolysis has ended, the cell contents are transferred together with toluene to a 50 ml round-bottom flask and the solvent is removed on a rotary evaporator at 50° C., 200-70 mbar, under reduced pressure. Unconverted reactant is recovered by means of short-path distillation (100° C., $10^3$ mbar).

Electrode material
Anode: boron-doped diamond (BDD) on Si
Cathode: Ni mesh
Electrolysis conditions:
Temperature [T]: 50° C.
Current [I]: 15 mA
Current density [j]: 2.8 mA/cm$^2$
Charge [Q]: 2 F/mol of deficiency component
Terminal voltage [$U_{max}$]: 3-5 V The biaryls were synthesized by the general method described above, and in a reaction apparatus as shown in FIG. 1.

The compounds according to the invention have a 2,3'-biphenol unit as central unit.

2,5'-Dihydroxy-4',5-dimethoxy-2'-methylbiphenyl

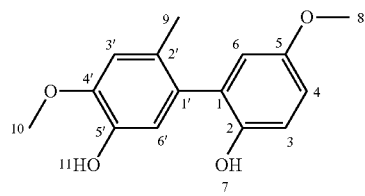

1.66 g (12 mmol, 1.0 equiv.) of 4-methylguaiacol and 4.49 g (36 mmol, 3.0 equiv.) of 4methoxyphenol were dissolved in 80 ml of HFIP, 1.63 g of MTES were added and the electrolyte was transferred to the electrolysis cell. After the electrolysis, the solvent and unconverted amounts of reactant are removed under reduced pressure, the crude product is purified by flash chromatography on silica gel 60 in a 4:1 eluent (cyclohexane:ethyl acetate) and the product is obtained as a colourless solid.

Yield: 2.05 g (66%, 7.9 mmol)
GC (hard method, HP-5): $t_R$=14.03 min
$R_f$(CH:EA=4:1)=0.33
$m_p$=118.7° C. (recrystallized from DCM/CH)
$^1$H NMR (600 MHz, DMSO) δ=2.01 (s, 3H, 9-H), 3.66 (s, 3H, 8-H), 3.77 (s, 3H, 10-H), 6.53 (d, 1H, 6-H), 6.55 (s, 1H, 6'-H), 6.72 (dd, 1H, 4-H), 6.77 (s, 1H, 3'-H), 6.79 (d, 1H, 3-H), 8.73 (s, 1H, 11-H), 8.75 (s, 1H, 7-H);
Couplings: $^3J_{3\text{-}H,\ 4\text{-}H}$=8.7 Hz; $^4J_{4\text{-}H,\ 6\text{-}H}$=3.0 Hz
$^{13}$C NMR (151 MHz, DMSO) δ=19.33 (C-9), 55.32 (C-8), 55.73 (C-10), 113.24 (C-4), 113.75 (C-3'), 115.99 (C-3), 116.07 (C-6), 117.40 (C-6'), 126.56 (C-2'), 129.06 (C-1), 130.95 (C-1'), 143.80 (C-5'), 146.52 (C-4'), 148.29 (C-2), 151.81 (C-5).

HRMS for $C_{15}H_{16}O_4$(ESI+) [M+Na$^+$]: calc. 283.0946, found. 283.0942.
MS (EI, GCMS): m/z (%): 260 (100) [M]$^{+\bullet}$, 245 (12) [M-CH$_3^\bullet$]$^+$.
Elemental analysis for $C_{15}H_{16}O_4$: calc. 69.22%; H, 6.20%, found. C, 69.02%; H, 6.34%.

3,4'-di-tert-butyl-5,6'-dimethoxy-[1,1'-biphenyl]-2,3'-diol

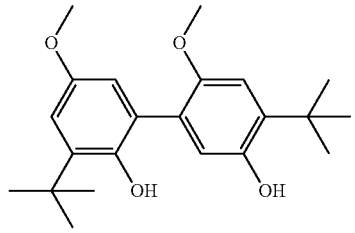 [SMILES: COc1cc(-c2cc(O)c(C(C)(C)C)cc2OC)c(O)c(C(C)(C)C)c1]

The synthesis was effected according to the general method above. After purification by column chromatography, the product was obtained in 15% yield.

For an alternative preparation route see: Anwar A. Hamama, Wassef W. Nawar Journal of Agricultural and Food Chemistry 1991, 36, 1063-1069.

The compounds according to the invention may have 2,2'-biphenol units as outer units.

2,2'-Dihydroxy-4',5-dimethyl-5'-(methylethyl)-3-methoxybiphenyl

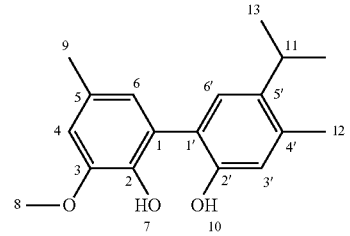

0.69 g (5 mmol, 1.0 equiv.) of 4-methylguaiacol and 2.28 g (15 mmol, 3.0 equiv.) of 3-methyl-4-(methylethyl)phenol were dissolved in 33 ml of 1,1,1,3,3,3-hexafluoroisopropanol (HFIP), 0.68 g of methyltriethylammonium methylsulphate (MTES) were added and the electrolyte was transferred to the electrolysis cell. After the electrolysis, the solvent and unconverted amounts of reactant are removed under reduced pressure, the crude product is purified by flash chromatography on silica gel 60 in a 9:1 eluent (cyclohexane:ethyl acetate) and the product is obtained as a colourless solid.

Yield: 716 mg (50%, 2.5 mmol)
GC (hard method, HP-5): $t_R$=14.87 min
$R_f$(CH:EA=4:1)=0.43
$m_p$=126.8° C. (recrystallized from CH)
$^1$H NMR (600 MHz, DMSO) δ=1.17-1.12 (m, 6H, 13-H), 2.24 (m, 6H, 9-H/12-H), 3.01 (dt, 1H, 11-H), 3.79 (s, 3H, 8-H), 6.55 (s, 1H, 6-H), 6.66 (d, 1H, 6'-H), 6.73 (d, 1H, 4-H), 6.96 (s, 1H, 3'-H), 8.16 (s, 1H, 7-H), 8.84 (s, 1H, 10-H);

Couplings: $^4J_{4\text{-}H,\ 6\text{-}H}$=2.2 Hz, $^4J_{6'\text{-}H,\ 11\text{-}H}$=2.9 Hz, $^3J_{11\text{-}H,\ 13\text{-}H}$=6.8 Hz;

$^{13}$C NMR (151 MHz, DMSO) δ=18.73, 20.80 (C-9/C-12), 23.54 (C-13), 28.10 (C-11), 55.78 (C-8), 111.23 (C-4), 117.34 (C-6'), 123.42 (C-1'), 123.49 (C-6), 126.43 (C-1), 127.36 (C-5), 127.49 (C-3'), 134.40 (C-5'), 136.62 (C-4'), 141.12 (C-2), 147.65 (C-3), 151.69 (C-2').

HRMS for $C_{18}H_{22}O_3$(ESI+) [M+Na$^+$]: calc. 309.1467, found. 309.1457.

MS (EI, GCMS): m/z (%): 286 (50) [M]$^{+\bullet}$, 271 (100) [M-CH$_3$]$^+$, 244 (22) [M-C$_3$H$_6^\bullet$]$^+$.

Elemental analysis for $C_{18}H_{22}O_3$: calc. C, 75.50%; H, 7.74%; found. C, 75.01%; H, 7.70%.

2,2'-Dihydroxy-5,5'-dimethyl-3-methoxybiphenyl

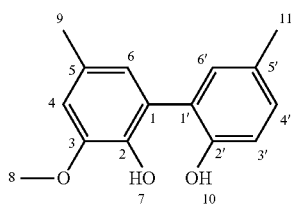

1.66 g (12 mmol, 1.0 equiv.) of 4-methylguaiacol and 3.91 g (36 mmol, 3.0 equiv.) of 4methylphenol were dissolved in 65 ml of HFIP and 14 ml of MeOH, 1.63 g of methyltriethylammonium methylsulphate (MTES) were added and the electrolyte was transferred to the electrolysis cell. After the electrolysis, the solvent and unconverted amounts of reactant are removed under reduced pressure, the crude product is purified by flash chromatography on silica gel 60 in a 4:1 eluent (cyclohexane:ethyl acetate) and the product is obtained as a colourless solid.

Yield: 440 mg (36%, 1.8 mmol)

GC (hard method, HP-5): $t_R$=13.56 min $R_f$(CH:EA=4:1)=0.38

$m_p$=162.0° C. (recrystallized from CH)

$^1$H NMR (400 MHz, DMSO) δ=2.18 (s, 3H, 9-H/11-H), 2.21 (s, 3H, 9-H/11-H), 3.76 (s, 3H, 8-H), 6.53 (s, 1H, 6-H), 6.71 (s, 1H, 4-H), 6.75 (d, 1H, 3'-H), 6.86-6.94 (m, 2H, 4'-H/6'-H), 8.53 (bs, 1H, 7-H/12-H);

Couplings: $^3J_{3'\text{-}H,\ 4'\text{-}H}$=8.4 Hz;

$^{13}$C NMR (101 MHz, DMSO) δ=20.21, 20.77 (C-9/C-11), 55.79 (C-8), 111.36 (C-4), 115.69 (C-3'), 123.50 (C-6), 125.72 (C-1'), 126.16 (C-1), 127.20 (C-5), 127.30 (C-5'), 128.50 (C-6'), 131.83 (C-4'), 141.20 (C-2), 147.61 (C-3), 152.11 (C-2').

HRMS for $C_{15}H_{16}O_3$(ESI+) [M+Na$^+$]: calc. 267.0997, found. 267.0999.

MS (EI, GCMS): m/z (%): 244 (100) [M]$^{+\bullet}$, 229 (64) [M-CH$_3^\bullet$]$^+$.

Elemental analysis for $C_{15}H_{16}O_3$: calc. C, 73.75%; H, 6.60%; found. C, 73.81%; H, 6.54%.

2,2'-Dihydroxy-3-methoxy-3',5,5'-trimethylbiphenyl

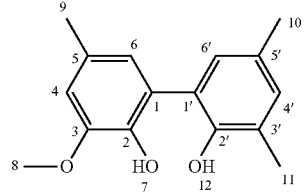

0.70 g (6 mmol, 1.0 equiv.) of 4-methylguaiacol and 2.08 g (17 mmol, 3.0 equiv.) of 2,4dimethylphenol were dissolved in 27 ml of HFIP and 6 ml of MeOH, 0.68 g of methyltriethylammonium methylsulphate (MTES) was added and the electrolyte was transferred to the electrolysis cell. After the electrolysis, the solvent and unconverted amounts of reactant are removed under reduced pressure, the crude product is purified by flash chromatography on silica gel 60 in a 9:1 eluent (cyclohexane:ethyl acetate) and the product is obtained as a pale yellow solid.

Yield: 663 mg (45%, 2.5 mmol)

GC (hard method, HP-5): $t_R$=13.97 min $R_f$(CH:EA=4:1)=0.29

$m_p$=119.7° C. (recrystallized from DCM/CH)

$^1$H NMR (400 MHz, CDCl$_3$) δ=2.34 (s, 3H, 10-H), 2.35 (s, 3H, 11-H), 2.38 (s, 3H, 9-H), 3.94 (s, 3H, 8-H), 6.16 (s, 1H, 12-H), 6.20 (s, 1H, 7-H), 6.76 (d, 1H, 4-H), 6.78 (d, 1H, 6-H), 6.98 (d, 1H, 6'-H), 7.03 (d, 1H, 4'-H);

Couplings: $^4J_{4\text{-}H,\ 6\text{-}H}$=1.7 Hz, $^4J_{4'\text{-}H,\ 6'\text{-}H}$=2.1 Hz;

$^{13}$C NMR (101 MHz, CDCl$_3$) δ=16.51 (C-9), 20.54 (C-10), 21.20 (C-11), 56.12 (C-8), 110.92 (C-4), 123.95 (C-6), 124.13 (C-1), 124.64 (C-1'), 126.18 (C-3'), 128.82 (C-6'), 129.59 (C-5'), 130.40 (C-5), 131.40 (C-4'), 139.46 (C-2), 146.35 (C-3), 149.42 (C-2').

HRMS for $C_{18}H_{16}O_3$(ESI+) [M+Na$^+$]: calc. 281.1154, found. 281.1152.

MS (EI, GCMS): m/z (%): 242 (100) [M]$^{+\bullet}$, 227 (38) [M-CH$_3^\bullet$]$^+$.

Elemental analysis for $C_{16}H_{18}O_3$: calc. C, 68.31%; H, 6.45%; found. C, 68.29%; H, 6.40%.

2,2'-Dihydroxy-3-methoxy-5-methyl-4'-(methyl-4'-(dimethylethyl)biphenyl

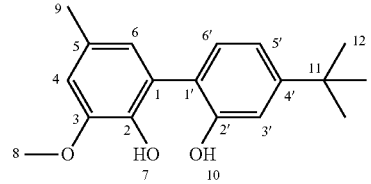

0.69 g (5 mmol, 1.0 equiv.) of 4-methylguaiacol and 2.25 g (15 mmol, 3.0 equiv.) of 3-tert-butylphenol were dissolved in 33 ml of HFIP, 0.68 g of methyltriethylammonium methylsulphate (MTES) was added and the electrolyte was transferred to the electrolysis cell. After the electrolysis, the solvent and unconverted amounts of reactant are removed under reduced pressure, the crude product is purified by flash chromatography on silica gel 60 in a 4:1 eluent (cyclohexane:ethyl acetate) and the product is obtained as a colourless solid.

Yield: 808 mg (63%, 3.1 mmol)
GC (hard method, HP-5): $t_R$=13.97 min
$R_f$(CH:EA=4:1)=0.29
$m_p$=160.3° C. (recrystallized from DCM/CH)
$^1$H NMR (400 MHz, CDCl$_3$) δ=1.37 (s, 9H, 12-H), 2.36 (s, 3H, 9-H), 3.94 (s, 3H, 8-H), 6.25 (s, 1H, 7-H), 6.48 (s, 1H, 10-H), 6.75 (d, 1H, 6-H), 6.79 (d, 1H, 4-H), 7.08 (dd, 1H, 5'-H), 7.12 (d, 1H, 3'-H), 7.27 (d, 1H, 6'-H);
Couplings: $^4J_{4-H, 6-H}$=1.7 Hz; $^3J_{5'-H, 6'-H}$=8.0 Hz, $^4J_{3'-H, 5'-H}$=1.7 Hz;
$^{13}$C NMR (101 MHz, CDCl$_3$) δ=21.24 (C-9), 31.31 (C-12), 34.58 (C-11), 56.15 (C-8), 110.79 (C-4), 114.94 (C-3'), 118.30 (C-5'), 122.37 (C-1'), 123.88 (C-1), 123.94 (C-6), 130.45 (C-6'), 130.53 (C-4'), 139.24 (C-5), 146.32 (C-3), 152.91 (C-2'), 153.13 (C-2).
HRMS for C$_{15}$H$_{16}$O$_4$(ESI+) [M+Na$^+$]: calc. 309.1467, found. 309.1466 MS (EI, GCMS): m/z (%): 242 (100) [M]$^{+•}$, 227 (38) [M-CH$_3$]$^+$.
Elemental analysis for C$_{18}$H$_{22}$O$_3$: calc. 75.50%; H, 7.74%; found. C, 75.41%; H, 7.72%.

2,2'-Dihydroxy-4',5-dimethy-3-methoxylbiphenyl 0.70 g (5 mmol, 1.0 equiv.) of 4-methylguaiacol and 1.65 g (15 mmol, 3.0 equiv.) of 3methylphenol were dissolved in 33 ml of HFIP, 0.68 g of methyltriethylammonium methylsulphate (MTES) was added and the electrolyte was transferred to the electrolysis cell. After the electrolysis, the solvent and unconverted amounts of reactant are removed under reduced pressure, the crude product is purified by flash chromatography on silica gel 60 in a 4:1 eluent (cyclohexane:ethyl acetate) and two cross-coupling products are obtained as colourless solids.

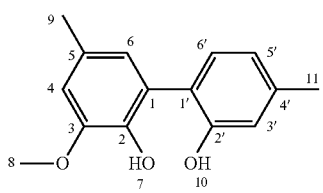

Yield: 266 mg (21%, 1.1 mmol)
GC (hard method, HP-5): $t_R$=13.72 min
$R_f$(CH:EA=4:1)=0.25
$m_p$=136.2° C. (recrystallized from DCM/CH)
$^1$H NMR (400 MHz, CDCl$_3$) δ=2.35 (s, 3H, 9-H/11-H), 2.37 (s, 3H, 9-H/11-H), 3.94 (s, 3H, 8-H), 6.17 (s, 1H, 10-H), 6.35 (s, 1H, 2-H), 6.74 (d, 1H, 4-H), 6.76 (s, 1H, 6-H), 6.88-6.83 (m, 1H, 5'-H), 6.90 (d, 1H, 3'-H), 7.21 (d, 1H, 6'-H);
Couplings: $^4J_{4-H, 6-H}$=1.8 Hz, $^3J_{5'-H, 6'-H}$=7.7 Hz, $^4J_{3'-H, 5'-H}$=1.5 Hz;
$^{13}$C NMR (101 MHz, CDCl$_3$) δ=21.11, 21.20 (C-9/C-11), 56.13 (C-8), 110.81 (C-4), 118.25 (C-3'), 121.97 (C-5'), 122.39 (C-1), 123.77 (C-1'), 123.85 (C-6), 130.50 (C-5), 130.68 (C-6'), 139.30 (C-4'), 139.54 (C-2), 146.31 (C-3), 153.33 (C-2').
HRMS for C$_{15}$H$_{16}$O$_3$(ESI+) [M+Na$^+$]: calc. 267.0997, found. 267.1006 MS (EI, GCMS): m/z (%): 244 (100) [M]$^{+•}$, 229 (18) [M-CH$_3$$^•$]$^+$. Elemental analysis for C$_{15}$H$_{16}$O$_3$: calc. C, 73.75%; H, 6.60%; found. C, 73.70%; H, 6.68%.

2,2'-Dihydroxy-3-methoxy-4'-5,5'-trimethylbiphenyl

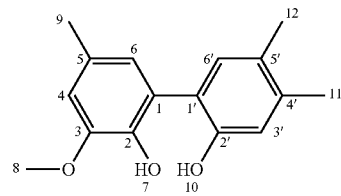

0.69 g (5 mmol, 1.0 equiv.) of 4-methylguaiacol and 1.83 g (15 mmol, 3.0 equiv.) of 3,4dimethylphenol were dissolved in 27 ml of HFIP and 6 ml of MeOH, 0.68 g of methyltriethylammonium methylsulphate (MTES) was added and the electrolyte was transferred to the electrolysis cell. After the electrolysis, the solvent and unconverted amounts of reactant are removed under reduced pressure, the crude product is purified by flash chromatography on silica gel 60 in a 9:1 eluent (cyclohexane:ethyl acetate) and the product is obtained as a colourless solid.

Yield: 688 mg (52%, 2.6 mmol)
GC (hard method, HP-5): $t_R$=14.52 min
$R_f$(CH:EA=4:1)=0.29
$m_p$=152.3° C. (recrystallized from DCM/CH)
$^1$H NMR (400 MHz, CDCl$_3$) δ=12.25 (s, 3H, 11-H), 2.28 (s, 3H, 12-H), 2.36 (s, 3H, 9-H), 3.93 (s, 3H, 8-H), 6.19 (s, 1H, 7-H), 6.25 (s, 1H, 10-H), 6.73 (d, 1H, 4-H), 6.76 (s, 1H, 6-H), 6.88 (s, 1H, 3'-H), 7.08 (s, 1H, 6'-H);
Couplings: $^4J_{4-H, 6-H}$=1.7 Hz;
$^{13}$C NMR (101 MHz, CDCl$_3$) δ=18.89 (C-11), 19.60 (C-12), 21.24 (C-9), 56.14 (C-8), 110.74 (C-4), 118.93 (C-3'), 122.54 (C-1), 123.82 (C-6), 123.97 (C-1'), 129.03 (C-5), 130.46 (C-4'), 131.69 (C-6'), 137.94 (C-5'), 139.26 (C-2), 146.31 (C-3), 151.36 (C-2').
HRMS for C$_{16}$H$_{18}$O$_3$(ESI+) [M+Na$^+$]: calc. 281.1154, found. 281.1157.
MS (EI, GCMS): m/z (%): 258 (100) [M]$^{+•}$, 243 (10) [M-CH$_3$$^•$]$^+$.
Elemental analysis for C$_{16}$H$_{18}$O$_3$: calc. 74.39%; H, 7.02%; found. C, 74.32%; H, 7.20%.

2,2'-Dihydroxy-5'-isopropyl-3-methoxy-5-methylbiphenyl

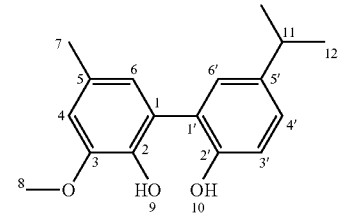

0.69 g (5 mmol, 1.0 equiv.) of 4-methylguaiacol and 2.05 g (15 mmol, 3.0 equiv.) of 4isopropylphenol were dissolved in 27 ml of HFIP and 6 ml of MeOH, 0.68 g of methyltriethylammonium methylsulphate (MTES) was added and the electrolyte was transferred to the electrolysis cell. After the electrolysis, the solvent and unconverted amounts of reactant are removed under reduced pressure, the crude product is purified by flash chromatography on silica gel 60 in a 4:1 eluent (cyclohexane:ethyl acetate) and the product is obtained as a brownish oil.

Yield: 0.53 g (39 mmol; 1.9%).

GC (hard method, HP-5): $t_R$=14.23 min $R_f$(CH:EA=4:1)=0.30

$^1$H NMR (400 MHz, CDCl$_3$) δ=1.27 (m, 6H), 2.36 (s, 3H), 2.91 (dt, J=13.8, 6.9, 6.9 Hz, 1H), 3.94 (s, 3H), 6.13-6.27 (m, 2H), 6.82-6.65 (m, 1H), 6.25 (m, 2H), 6.75 (s, 1H), 6.77 (s, 1H), 6.99 (d, J=8.1 Hz, 1H), 7.19-7.12 (m, 2H);

$^{13}$C NMR (101 MHz, CDCl$_3$) δ=21.25, 24.27, 33.40, 56.18, 110.92, 117.60, 123.91, 124.23, 125.07, 127.29, 128.80, 130.57, 139.29, 141.42, 146.31, 151.51.

HRMS for C$_{17}$H$_{20}$O$_3$(ESI+) [M+Na$^+$]: calc. 295.1310, found. 295.1297.

MS (EI, GCMS): m/z (%): 272 (80) [M]$^{+\bullet}$, 257 (100) [M-CH$_3^\bullet$]$^+$.

2,2'-Dihydroxy-3-methoxy-5-methyl-5'-tert-butylbiphenyl

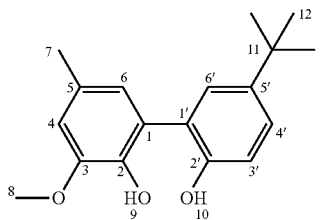

0.69 g (5 mmol, 1.0 equiv.) of 4-methylguaiacol and 2.26 g (15 mmol, 3.0 equiv.) of 4-tert-butylphenol were dissolved in 27 ml of HFIP and 6 ml of MeOH, 0.68 g of methyltriethylammonium methylsulphate (MTES) was added and the electrolyte was transferred to the electrolysis cell. After the electrolysis, the solvent and unconverted amounts of reactant are removed under reduced pressure, the crude product is purified by flash chromatography on silica gel 60 in a 4:1 eluent (cyclohexane:ethyl acetate) and the product is obtained as a yellowish oil.

Yield: 0.48 g (34%, 1.7 mmol)

GC (hard method, HP-5): $t_R$=14.52 min $R_f$(CH:EA=4:1)=0.24

$^1$H NMR (400 MHz, CDCl$_3$) δ=1.34 (s, 9H), 2.37 (s, 3H), 3.94 (s, 3H), 6.17 (s, 1H), 6.24 (s, 1H), 6.75 (s, 1H), 6.77 (s, 1H), 6.99 (d, J=8.4 Hz, 1H), 7.31-7.29 (m, 1H), 7.33 (dd, J=8.4, 2.5 Hz, 1H).

$^{13}$C NMR (101 MHz, CDCl$_3$) δ=21.28, 31.61, 34.20, 56.18, 110.91, 117.25, 123.92, 124.41, 124.63, 126.38, 127.78, 130.58, 139.32, 143.70, 146.32, 151.22.

HRMS for C$_{18}$H$_{22}$O$_3$(ESI+) [M+Na$^+$]: calc. 309.1467, found. 309.1476.

MS (EI, GCMS): m/z (%): 286 (28) [M]$^{+\bullet}$, 271 (100) [M-CH$_3^\bullet$]$^+$.

2,2'-Dihydroxy-3',5'-di-tert-butyl-5-methyl-3-methoxybiphenyl

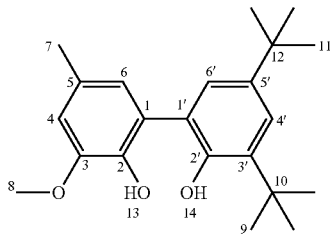 [SMILES: COc1cc(C)cc(-c2cc(C(C)(C)C)cc(C(C)(C)C)c2O)c1O]

0.69 g (5 mmol, 1.0 equiv.) of 4-methylguaiacol and 3.12 g (15 mmol, 3.0 equiv.) of 2,4-di-tert-butylphenol were dissolved in 27 ml of HFIP and 6 ml of MeOH, 0.68 g of methyltriethylammonium methylsulphate (MTES) was added and the electrolyte was transferred to the electrolysis cell. After the electrolysis, the solvent and unconverted amounts of reactant are removed under reduced pressure, the crude product is purified by flash chromatography on silica gel 60 in a 9:1 eluent (cyclohexane:ethyl acetate) and the product is obtained as a colourless solid.

Yield: 0.41 g (24%, 1.2 mmol)

GC (hard method, HP-5): $t_R$=15.15 min $R_f$(CH:EA=9:1)=0.35

$m_p$=120.2° C. (recrystallized in n-pentane)

$^1$H NMR (400 MHz, CDCl$_3$) δ=1.36 (s, 9H), 1.50 (s, 9H), 2.38 (s, 3H), 3.96 (s, 3H), 6.00 (s, 1H), 6.05 (s, 1H), 6.77 (s, 1H), 7.16 (d, J=2.5 Hz, 1H), 7.39 (d, J=2.5 Hz, 1H).

$^{13}$C NMR (101 MHz, CDCl$_3$) δ=21.23, 29.88, 31.69, 34.40, 35.23, 56.17, 111.03, 123.96, 124.17, 125.09, 125.50, 130.42, 136.73, 139.72, 142.36, 146.45, 149.82.

MS (EI, GCMS): m/z (%): 342 (22) [M]$^{+\bullet}$, 327 (100) [M-CH$_3^\bullet$]$^+$.

2,2'-Dihydroxy-3',5-dimethyl-3-methoxy-5'-tert-butylbiphenyl

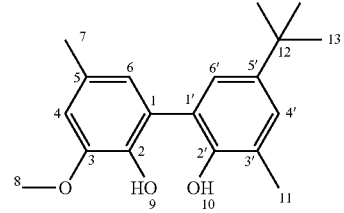 [SMILES: COc1cc(C)cc(-c2cc(C(C)(C)C)cc(C)c2O)c1O]

0.69 g (5 mmol, 1.0 equiv.) of 4-methylguaiacol and 2.47 g (15 mmol, 3.0 equiv.) of 2-methyl-4-tert-butylphenol were dissolved in 27 ml of HFIP and 6 ml of MeOH, 0.68 g of methyltriethylammonium methylsulphate (MTES) was added and the electrolyte was transferred to the electrolysis cell. After the electrolysis, the solvent and unconverted amounts of reactant are removed under reduced pressure, the crude product is purified by flash chromatography on silica gel 60 in a 4:1 eluent (cyclohexane:ethyl acetate) and the product is obtained as a yellowish oil.

Yield: 0.69 g (46%, 2.3 mmol)

GC (hard method, HP-5): $t_R$=14.79 min $R_f$(CH:EA=4:1)=0.33

¹H NMR (400 MHz, CDCl₃) δ=1.37 (s, 9H), 2.39 (d, J=2.4 Hz, 6H), 3.94 (s, 3H), 6.15 (s, 1H), 6.17 (s, 1H), 6.77 (s, 1H), 6.79 (s, 1H), 7.17 (d, J=2.5 Hz, 1H), 7.24 (d, J=2.4 Hz, 1H);
¹³C NMR (101 MHz, CDCl₃) δ=16.90, 21.28, 31.67, 34.12, 56.16, 110.94, 124.02, 124.17, 124.59, 125.41, 125.65, 127.86, 130.47, 139.50, 143.07, 146.40, 149.41.
MS (EI, GCMS): m/z (%): 300 (18) [M]⁺·, 285 (100) [M-CH₃·]⁺.

2,2'-Dihydroxy-3-methoxy-5-methyl-5'-(1-methylethyl)biphenyl

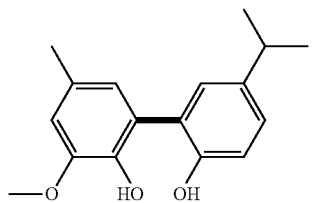

0.69 g (5 mmol, 1.0 eq.) of 4-methylguaiacol and 2.05 g (15 mmol, 3.0 eq.) of 4-isopropylphenol and 0.68 g of methyltriethylammonium methylsulphate (MTES) in 27 ml of HFIP+6 ml of MeOH were added to methyltriethylammonium methylsulphate (MTES) and the electrolyte was transferred to the electrolysis cell. After the electrolysis, the solvent and unconverted amounts of reactant are removed under reduced pressure, the crude product is purified by flash chromatography on silica gel 60 in a 4:1 eluent (cyclohexane:ethyl acetate) and the product is obtained as a brownish oil.

Yield: 39 g (1.9 mmol; 18%).

R_f(cyclohexane:ethyl acetate=4:1)=0.30; ¹H NMR (400 MHz, CDCl₃) δ=1.27 (m, 6H), 2.36 (s, 3H), 2.91 (sept, J=6.9 Hz, 1H), 3.94 (s, 3H), 6.13-6.27 (m, 2H), 6.65-6.82 (m, 2H), 6.99 (d, J=8.1 Hz, 1H), 7.12-7.19 (m, 2H); ¹³C NMR (101 MHz, CDCl₃) δ=21.37, 24.39, 33.53, 56.31, 111.04, 117.73, 124.04, 124.36, 125.20, 127.42, 128.93, 130.70, 139.42, 141.55, 146.44, 151.64. HRMS for C₁₇H₂₀O₃(ESI+) [M+Na⁺]: calculated. 295.1310, found. 295.1297; MS (EI, GCMS): m/z (%): 272 (80) [M]⁺·, 257 (100) [M-CH₃·]⁺.

2,2'-Dihydroxy-3-methoxy-5-methyl-4'-(methylethyl)biphenyl

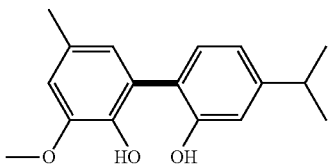

0.69 g (5 mmol, 1.0 eq.) of 4-methylguaiacol and 2.065 g (15 mmol, 3.0 eq.) of 3-isopropylphenol and 0.68 g of methyltriethylammonium methylsulphate (MTES) were dissolved in 33 ml of HFIP and the electrolyte was transferred to the electrolysis cell. After the electrolysis, the solvent and unconverted amounts of reactant are removed under reduced pressure, the crude product is purified by flash chromatography on silica gel 60 in a 4:1 eluent (cyclohexane:ethyl acetate) and the product is obtained as a brownish oil (yield: 52%, 705 mg, 2.6 mmol).

R_f(cyclohexane:ethyl acetate=4:1)=0.29; ¹H NMR (400 MHz, CDCl₃) δ=1H NMR (400 MHz, CDCl3) δ 1.27 (s, 3H), 1.29 (s, 3H), 2.34 (s, 3H), 2.91 (sept, J=7.0 Hz, 1H), 3.94 (s, 3H), 6.15 (s, 1H), 6.35 (s, 1H), 6.73 (d, J=1.8 Hz, 1H), 6.75-6.77 (m, 1H), 6.90 (dd, J=7.9 Hz, 1.8 Hz, 1H), 6.94 (d, J=1.7 Hz, 1H), 7.23 (d, J=7.8 Hz, 1H). ¹³C NMR (101 MHz, CDCl₃) δ=21.36, 24.02, 33.92, 56.30, 77.16, 110.91, 115.77, 119.56, 122.81, 124.00, 124.08, 130.65, 130.84, 139.38, 146.43, 150.72, 153.54. HRMS for C₁₇H₂₀O₃(ESI+) [M+Na⁺]: calculated. 295.1310, found. 295.1305; MS (EI, GCMS): m/z (%): 272 (100) [M]⁺·, 257 (50) [M-CH₃·]⁺. Elemental analysis for C₁₇H₂₀O₃: calculated 74.97%; H, 7.40%; found. C, 75.05%; H, 7.36%.

2,2'-Dihydroxy-4',5-dimethyl-3-methoxybiphenyl 0.28 g (2 mmol, 1.0 eq.) of 4-methylguaiacol, 1.22 g (6 mmol, 3.0 eq.) of 3-methylphenol and 0.77 g of MTBS were dissolved in 25 ml of HFIP and the electrolyte was transferred to the beaker-type electrolysis cell. After the electrolysis, the solvent and unconverted amounts of reactant are removed under reduced pressure, the crude product is purified by flash chromatography on silica gel 60 in a 4:1 eluent (cyclohexane:ethyl acetate) and this led to the two cross-coupling products as a colourless and viscous oil.

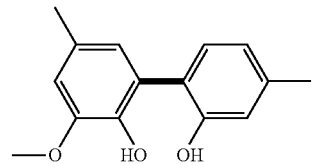

Yield: 21%, 266 mg, 1.1 mmol; R_f(cyclohexane:ethyl acetate=4:1)=0.25; m_p=136.2° C. (crystallized from dichloromethane/cyclohexane); ¹H NMR (400 MHz, CDCl₃) δ=2.35 (s, 3H), 2.37 (s, 3H), 3.94 (s, 3H), 6.17 (s, 1H), 6.35 (s, 1H), 6.74 (d, J=1.8 Hz, 1H), 6.76 (s, 1H), 6.886.83 (m, 1H), 6.90 (d, 1H, J=1.5 Hz), 7.21 (d, 1H, J=7.7 Hz); ¹³C NMR (101 MHz, CDCl₃) δ=21.11, 21.20 56.13, 110.81, 118.25, 121.97, 122.39, 123.77, 123.85, 130.50, 130.68, 139.30, 139.54, 146.31, 153.33. HRMS for C₁₅H₁₆O₃(ESI+) [M+Na⁺]: calculated. 267.0997, found. 267.1006; MS (EI, GCMS): m/z (%): 244 (100) [M]⁺·, 229 (18) [M-CH₃·]⁺·. Elemental analysis for C₁₅H₁₆O₃: calculated. C, 73.75%; H, 6.60%; found. C, 73.70%; H, 6.68%.

2,2'-Dihydroxy-5,5'-dimethyl-3'-(1,1-dimethylethyl)-3-methoxybiphenyl

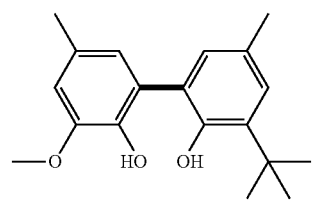

0.69 g (5 mmol, 1.0 eq.) of 4-methylguaiacol, 2.47 g (15 mmol, 3.0 eq.) of 4-methyl-2-tert-butylphenol and 0.68 g of methyltriethylammonium methylsulphate (MTES) were dissolved in 27 ml of HFIP+6 ml of MeOH and the electrolyte was transferred to the electrolysis cell. After the electrolysis, the solvent and unconverted amounts of reactant are removed under reduced pressure, the crude product is purified by flash chromatography on silica gel 60 in a 4:1 eluent (cyclohexane:ethyl acetate) and the product is obtained as a yellow oil (yield: 36%, 545 mg, 1.8 mmol).

$R_f$(cyclohexane:ethyl acetate=9:1)=0.36; $^1$H NMR (400 MHz, CDCl$_3$) δ=1.46 (s, 9H), 2.34 (m, 6H), 3.93 (s, 3H), 5.99 (s, 1H), 6.01 (s, 1H), 6.74 (s, 2H), 6.96 (d, J=1.9 Hz, 1H), 7.14 (d, J=1.9 Hz, 1H); $^{13}$C NMR (101 MHz, CDCl$_3$) δ=21.05, 21.32, 29.96, 35.05, 56.30, 77.16, 111.21, 124.18, 124.24, 125.92, 127.67, 129.15, 129.22, 130.51, 137.57, 139.87, 146.57, 150.10. HRMS for C$_{22}$H$_{30}$O$_3$(ESI+) [M+Na$^+$]: calculated. 323.1623, found. 323.1618; MS (EI, GCMS): m/z (%): 300 (100) [M]$^{+\bullet}$, 285 (100) [M-CH$_3^\bullet$]$^+$.

Synthesis of the Ligands 6,6'-((4',5-Dimethoxy-6'-methyl-[1,1'-biphenyl]-2,3'-diyl)bis(oxy))didibenzo[d,f][1,3,2]-dioxaphosphepin

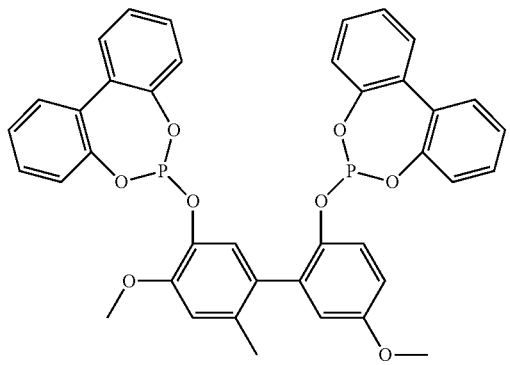

(1)

To a stirred suspension of 4',5-dimethoxy-6'-methyl-[1,1'-biphenyl]-2,3'-diol (0.602 g; 2.314 mmol) in toluene (13 ml) was added triethylamine (0.734 g; 7.254 mmol) and the mixture was cooled to 0° C. To this mixture was added dropwise a solution of 6-chlorodibenzo[d,f][1,3,2]dioxaphosphepin (1.418 g; 5.656 mmol) in toluene (18 ml). The reaction mixture was stirred at 0° C. for 1 h and at room temperature overnight. Then the mixture was stirred at 70° C. for 2 h and filtered through silica gel. The filtrate was concentrated to dryness under reduced pressure and the resulting residue was purified by column chromatography (dichloromethane/toluene, 1:1, $R_f$=0.5). Yield: 0.886 g (1.286 mmol; 56%).

Elemental analysis (calc. for C$_{39}$H$_{30}$O$_8$P$_2$=688.57 g/mol) C, 68.16 (68.02); H, 4.36 (4.39); P 8.96 (9.00) %.

$^{31}$P NMR (CD$_2$Cl$_2$): 145.7; 146.7 ppm.

$^1$H-NMR (CD$_2$Cl$_2$): 2.21 (m, 3H); 3.87 (s, 3H); 4.06 (s, 3H); 6.87 (m, 1H, H$_{arom}$); 6.92-7.14 (m, br, 4H, H$_{arom}$); 7.17 (m, 1H, H$_{arom}$); 7.28 (m, 1H, H$_{arom}$); 7.28-7.38 (m, 7H, H$_{arom}$); 7.38-7.42 (m, 2H, H$_{arom}$); 7.42-7.48 (m, 1H, H$_{arom}$); 7.49-7.61 (m, 4H, H$_{arom}$) ppm.

$^{13}$C NMR (CD$_2$Cl$_2$): 20.2; 21.6; 56.1; 56.6; 114.4 (d, J$_{CP}$=18.7 Hz); 117.0; 122.2 (d, J$_{CP}$=8.7 Hz); 122.6 (d, J$_{CP}$=14.2 Hz); 124.2 (d, J$_{CP}$=6.7 Hz); 125.8 (d, J$_{CP}$=4.6 Hz); 128.6; 129.4; 129.6 (d, J$_{CP}$=3.2 Hz); 130.3 (d, J$_{CP}$=7.3 Hz); 130.4; 131.5 (m); 134.5; 138.4; 138.7 (d, J$_{CP}$=6.5 Hz); 143.2 (d, J$_{CP}$=7.6 Hz); 149.4 (m); 150.8; 156.7 ppm.

ESI-TOF/HRMS: m/e 689.14883 (M+H)$^+$.

2,2'-((4',5-Dimethoxy-6'-methyl-[1,1'-biphenyl]-2,3'-diyl)bis(oxy))bis(4,4,5,5-tetraphenyl-1,3,2-dioxaphospholane)

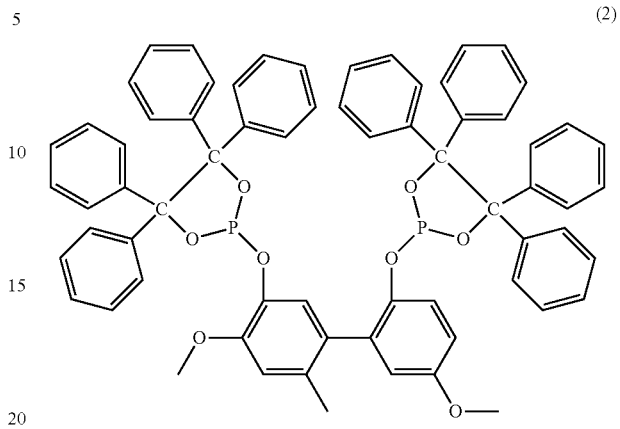

(2)

To a solution of 4',5-dimethoxy-6'-methyl-[1,1'-biphenyl]-2,3'-diol (0.335 g; 1.286 mmol) in THF (10 ml) were added 2 equivalents of n-butyllithium dissolved in hexane (4.83 ml) at −20° C. The mixture was stirred at −20° C. for 20 min and then a solution of 2-chloro-4,4,5,5-tetraphenyl-1,3,2-dioxaphospholane (1.109 g; 2.573 mmol) in THF (6 ml) was added at room temperature. The reaction mixture was stirred overnight and the solvent was drawn off under reduced pressure. Toluene (20 ml) was added and the resulting solution was filtered. The filtrate was concentrated to dryness under reduced pressure. The resulting solid was dried at 50° C./0.1 mbar for 3 h and then recrystallized from hot acetonitrile (26 ml). Yield: 0.602 g (0.574 mmol; 45%).

Elemental analysis (calc. for C$_{67}$H$_{54}$O$_8$P$_2$=1049.10 g/mol) C, 75.66 (76.71); H, 5.24 (5.19); P 6.17 (5.90) %.

$^{31}$P NMR (CD$_2$Cl$_2$): 140.6; 141.1 ppm.

$^1$H NMR (CD$_2$Cl$_2$): 1.99 (m, 3H); 3.80 (s, 3H); 3.90 (s, 3H); 6.50 (m, 1H, H$_{arom}$); 6.70 (m, 1H, H$_{arom}$); 6.86 (m, 1H, H$_{arom}$); 7.02-7.23 (m, 34H, H$_{arom}$); 7.41 (m, 4H, H$_{arom}$); 7.62 (m, 4H, H$_{arom}$) ppm.

$^{13}$C NMR (CD$_2$Cl$_2$, several regions in the aromatic range with signal overlaps): 20.1; 56.0; 56.8; 95.3; 95.5; 113.9; 114.5; 116.5; 122.4 (d, J$_{CP}$=8.5 Hz); 124.5; 127.4; 127.4; 127.5; 127.7; 129.2; 129.9; 130.1; 130.4; 130.7; 133.9; 134.9; 138.3 (d, J$_{CP}$=6.7 Hz); 142.5; 142.7; 142.9; 143.1; 143.1; 150.8 (d, J$_{CP}$=3.2 Hz); 156.3 ppm.

ESI-TOF/HRMS: m/e 1071.31785 (M+Na)$^+$.

6,6'-((3,4-Di-tert-butyl-5,6'-dimethoxy-[1,1'-biphenyl]-2,3'-diyl)bis(oxy))-dibenzo[d,f][1,3,2]dioxaphosphepin

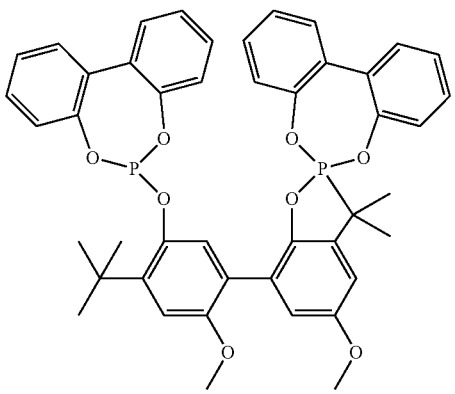

(3)

To a solution of 3,4'-di-tert-butyl-5,6'-dimethoxy-[1,1'-biphenyl]-2,3'-diol (0.505 g; 1.409 mmol) in toluene (10 ml) was added pyridine (0.251 g; 3.170 mmol), and the resulting mixture was added dropwise at 3° C. to a solution of 6-chlorodibenzo[d,f][1,3,2]dioxaphosphepin (0.777 g; 3.100 mmol) in toluene (10 ml). The reaction mixture was stirred overnight at room temperature and for 2 h at 70° C. The mixture was filtered through silica gel and the filtrate was concentrated to dryness under reduced pressure. The residue obtained was recrystallized from acetonitrile (13 ml). Elemental analysis (calc. for $C_{46}H_{44}O_8P_2$=786.79 g/mol) C, 70.30 (70.22); H, 5.78 (5.64); P 7.93 (7.87) %.

$^{31}$P NMR ($CD_2Cl_2$): 145.2 (d, $J_{PP}$=14.3 Hz); 147.4 (d, $J_{PP}$=14.3 Hz) ppm.

$^1$H NMR ($CD_2Cl_2$): 1.50 (s, 9H); 1.59 (s, 9H); 3.81 (m, 3H); 3.90 (m, 3H); 6.74 (m, 1H, $H_{arom}$); 6.78-6.82 (m, 1H, $H_{arom}$); 6.84-6.88 (m, 1H, $H_{arom}$); 6.96-7.01 (m, 1H, $H_{arom}$); 7.07 (m, 1H, $H_{arom}$); 7.11-7.18 (m, 2H, $H_{arom}$); 7.24 (m, 1H, $H_{arom}$); 7.26-7.35 (m, 7H, $H_{arom}$); 7.40 (m, 1H, $H_{arom}$); 7.43-7.53 (m, 4H, $H_{arom}$) ppm.

$^{13}$C NMR ($CD_2Cl_2$): 29.8; 30.9; 35.3; 35.8; 55.9; 56.1; 114.4; 115.0; 116.5; 120.0 (d, $J_{CP}$=9.6 Hz); 122.4; 122.6; 123.1; 125.5 (d, $J_{CP}$=4.5 Hz); 125.6; 129.3; 129.4 (d, $J_{CP}$=4.5 Hz); 129.7 (m); 129.9; 130.0; 130.1; 130.2; 131.3 (d, $J_{CP}$=2.9 Hz); 131.4; 131.5; 131.5; 131.5; 131.6; 131.6 (The latter six frequencies probably also result from C—P couplings. No assignment of individual signals has been made); 132.1 (d, $J_{CP}$=6.8 Hz); 140.3; 143.3 (d, $J_{CP}$=7.9 Hz); 143.7; 143.9 (d, $J_{CP}$=7.7 Hz); 149.3; 149.3; 149.4; 149.4; 149.5; 149.5; (The latter six frequencies probably also result from C—P couplings. No assignment of individual signals has been made.); 150.0 (d, $J_{CP}$=6.0 Hz); 155.6 (d, $J_{CP}$=15.6 Hz) ppm.

ESI-TOF/HRMS: m/e 787.25933 (M+H)$^+$.

2,2'-((3,4'-Di-tert-butyl-5,6'-dimethoxy-[1,1'-biphenyl]-2,3'-diyl)bis(oxy))bis(4,4,5,5-tetraphenyl-1,3,2-dioxaphospholane)

(4)

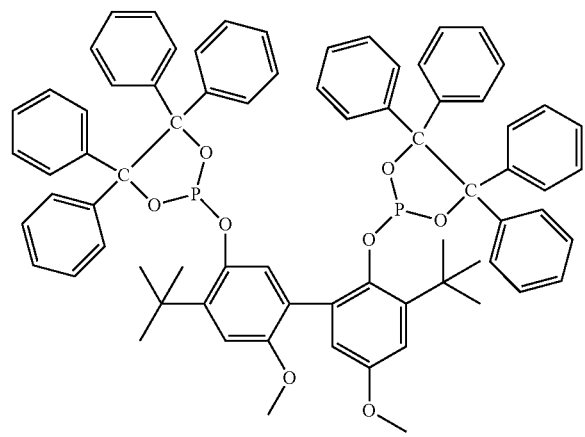

To a solution of 3,4'-di-tert-butyl-5,6'-dimethoxy-[1,1'-biphenyl]-2,3'-diol (0.357 g; 0.996 mmol) in THF (4.5 ml) were added, at −20° C., two equivalents of n-butyllithium in hexane (4 ml). The mixture was stirred at this temperature for another 20 min and then warmed to room temperature. A solution of 2-chloro-4,4,5,5-tetraphenyl-1,3,2-dioxaphospholane (0.858 g; 1.992 mmol) in THF (7 ml) was added. The reaction mixture was stirred overnight and the solvent was removed under reduced pressure. After adding toluene (20 ml), the resulting suspension was filtered through silica gel and the filtrate was concentrated to dryness under reduced pressure. The resulting yellow solid was dried at 50° C./0.1 mbar and then purified by means of column chromatography (hexane/dichloromethane, 1:1, $R_f$=0.5). Yield: 0.842 g (0.734 mmol; 77%). Elemental analysis (calc. for $C_{74}H_{68}O_8P_2$=1047.13 g/mol) C, 78.11 (78.00); H, 5.38 (5.39); P 6.02 (5.92) %.

$^{31}$P NMR ($CD_2Cl_2$): 140.0 (d, $J_{PP}$=25.9 Hz); 147.7 (d, $J_{PP}$=25.9 Hz) ppm.

$^1$H NMR ($CD_2Cl_2$): 1.11 (m, 9H); 1.33 (m, 9H); 3.77 (s, 3H); 3.86 (m, 3H); 6.57 (m, 1H, $H_{arom}$); 6.83 (m, 2H, $H_{arom}$); 6.90-7.01 (m, 8H, $H_{arom}$); 7.04-7.06 (m, 2H, $H_{arom}$); 7.06-7.11 (m, 10H, $H_{arom}$); 7.11-7.13 (m, 4H, $H_{arom}$); 7.13-7.15 (m, 3H, $H_{arom}$); 7.16-7.18 (m, 2H, $H_{arom}$); 7.20-7.24 (m, 3H, $H_{arom}$); 7.26-7.30 (m, 3H, $H_{arom}$); 7.35-7.42 (m, 2H, $H_{arom}$); 7.49-7.60 (m, 4H, $H_{arom}$) ppm.

$^{13}$C NMR ($CD_2Cl_2$): 29.8; 30.5; 35.0; 35.1; 55.7; 55.8; 94.5 (d, $J_{CP}$=8.3 Hz); 94.7 (d, $J_{CP}$=7.5 Hz); 94.9 (d, $J_{CP}$=8.3 Hz); 95.1 (d, $J_{CP}$=7.7 Hz); 114.0; 116.9 (d, $J_{CP}$=4.8 Hz); 120.5 (d, $J_{CP}$=10.2 Hz); overlapping signals from 127.0 to 129.5 ppm; 129.8; 130.0; 131.3; 132.7 (d, $J_{CP}$=9.2 Hz); 139.2; 139.7; 142.2 (d, $J_{CP}$=5.9 Hz); 142.6; 142.6; 142.7; 142.8; 142.8; 142.9; 142.9; 143.0; 143.4; 143.5; 144.0; 144.0; 144.1; 144.1 (signal overlaps for the latter 14 frequencies); 155.0 (d, $J_{CP}$=8.3 Hz); (d, $J_{CP}$=19.7 Hz) ppm.

ESI-TOF/HRMS: m/e 1169.42807 (M+Na)$^+$.

Procedure for the Catalysis Experiments

The hydroformylation was conducted in a 200 ml autoclave equipped with pressure-retaining valve, gas flow meter, sparging stirrer and pressure pipette from Premex Reactor AG, Lengau, Switzerland. To minimize the influence of moisture and oxygen, the toluene used as solvent was dried with sodium ketyl and distilled under argon. The following substrates used as substrate were heated at reflux over sodium and distilled under argon for several hours: 1-octene (Aldrich), cis/trans-2-pentene (Aldrich) and n-octenes (Oxeno GmbH, octene isomer mixture of 1-octene: ~3%; cis+trans-2-octene; ~49%; cis+trans-3-octene: ~29%; cis+trans-octene-4: ~16%; structurally isomeric octenes: ~3%).

For the experiments, the following solutions of rhodium in the form of [(acac)Rh(COD)](acac=acetylacetonate anion; COD=1,5-cyclooctadiene) (OMG AG & Co. KG, Hanau, D E) as the catalyst precursor were introduced into the autoclave in toluene under an argon atmosphere: for experiments at 100 ppm by mass of rhodium 10 ml of a 4.31 millimolar solution, for 40 ppm by mass the same amount of an appropriately diluted solution. The appropriate amount of the phosphite compound, generally 2 to 5 ligand equivalents per unit rhodium, dissolved in toluene was then added. By adding further toluene (the total mass of toluene was determined for the GC analysis, see below), the starting volume of the catalyst solution was adjusted to a) 41.0 ml in the case of intended addition of 15 ml of the olefin via the pressure pipette (1-octene, n-octenes and experiments with elevated 2-pentene concentration), or b) 51.9 ml in the case of intended addition of 4.1 ml of 2-pentene. The mass of toluene introduced was determined in each case. Starting weights of the olefins: 1-octene (10.62 g; 94.64 mmol), n-octenes (10.70 g; 95.35 mmol), 2-pentene 9.75 g; 139.00 mmol). The autoclave was heated while stirring (1500 rpm) to the temperatures stated in each case at a total gas pressure (synthesis gas: Linde; $H_2$ (99.999%): CO (99.997%)=1:1) of a) 42 bar for a final pressure of 50 bar; b) 12 bar for a final pressure of 20 bar and c) 7 bar for a final pressure of 10 bar. After reaching the reaction temperature, the synthesis gas pressure was increased to a) 48.5 bar for a final pressure of 50 bar, b) 19.5 bar for a final pressure of 20 bar and c) 9.5 bar for a final pressure of 10 bar and the olefin (mixture) specified in the table in each case was injected under a positive pressure of about 3 bar set in the pressure pipette.

The reaction was conducted at a constant pressure of 50, 20 or 10 bar (closed-loop pressure controller from Bronkhorst, the Netherlands) over 4 h. After the reaction time had elapsed, the autoclave was cooled to room temperature, decompressed while stirring and purged with argon. 1 ml of each reaction mixture was removed immediately after the stirrer had been switched off, diluted with 5 ml of pentane and analysed by gas chromatography: HP 5890 Series II plus, PONA, 50 m×0.2 mm×0.5 μm; residual olefin and aldehyde were determined quantitatively against the toluene solvent as internal standard.

Results of the Catalysis Experiments
Solvent: toluene
Yld.=yield
Sel.=selectivity
p=pressure in [bar]
T=temperature in [° C.]
t=time in [h]
[Rh]=rhodium concentration in [ppm]
L/Rh=ratio of ligand to rhodium Comparative ligands selected were the ligands A and B. They were prepared according to DE 10 2006 058 682 A1.

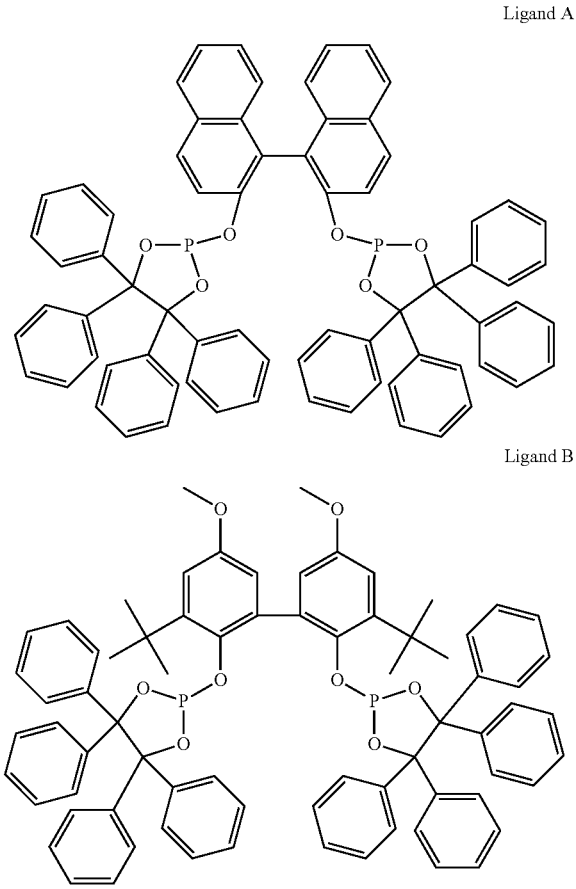

Ligand A

Ligand B

The inventive compounds are identified here by *.

TABLE 1

| | 1-Octene | | | | | | |
|---|---|---|---|---|---|---|---|
| Ligand | p (bar) | T (° C.) | t (h) | [Rh] (ppm) | L/Rh | Yld. (%) | Sel. (%) |
| 1* | 50 | 100 | 4 | 40 | 2 | 93 | 90.1 |
| 2* | 50 | 100 | 4 | 40 | 1 | 99 | 47.1 |
| 3* | 50 | 100 | 4 | 40 | 2 | 80 | 95.8 |

TABLE 1-continued

| | 1-Octene | | | | | | |
|---|---|---|---|---|---|---|---|
| Ligand | p (bar) | T (° C.) | t (h) | [Rh] (ppm) | L/Rh | Yld. (%) | Sel. (%) |
| 4* | 50 | 100 | 4 | 40 | 2 | 84 | 96.2 |
| A | 50 | 100 | 4 | 40 | 2 | 89 | 83 |

As can be inferred from Table 1, the inventive compounds are notable for very good yields in the hydroformylation of terminal olefins, more specifically 1-octene here. Compounds 1 and 2 have an improved yield compared to the comparative ligand A. Compounds 3 and 4, although they have slightly poorer yields than comparative ligand A, have much better selectivity.

The inventive compounds thus make it possible to improve the reaction either in terms of yield or in terms of selectivity, according to the appropriate choice of compound. The use of compound 1 even improves yield and selectivity.

TABLE 2

| | 2-Pentene | | | | | | |
|---|---|---|---|---|---|---|---|
| Ligand | p (bar) | T (° C.) | t (h) | [Rh] (ppm) | L/Rh | Yld. (%) | Sel. (%) |
| 1* | 20 | 120 | 4 | 100 | 1 | 100 | 54.9 |
| 1* | 20 | 120 | 4 | 100 | 0.5 | 96 | 57.5 |
| 3* | 20 | 120 | 4 | 100 | 2 | 93 | 83.3 |
| B | 20 | 120 | 4 | 100 | 2 | 14 | 99 |

With comparative ligand B, a very good selectivity of 99% was achieved for 2-pentene, but the yield at 14% is so low that the use of such a ligand is only of little interest for an industrial scale process. The space-time yields with this ligand are so poor that this opposes the use of the comparative ligand B from an economic point of view.

The inventive compounds all have a very good yield in combination with an acceptable to good selectivity.

In addition, it is possible to set a low phosphorus/rhodium ratio—P/Rh for short—in the reaction. This is of particular relevance since the ligands can make up a large portion of the process costs. Thus, if less ligand is required, this has an immediate positive effect on the overall economic viability of the industrial scale process.

As the experimental results show, the stated problem is solved by the inventive compounds.

It has been possible for the first time to provide bisphosphites which have a central 2,3'-biphenol unit and which have good to very good hydroformylation properties. This has been demonstrated by the examples shown.

Such specific structures and ligands of this kind were entirely unknown and unobtainable to date.

The special feature here is that a central 2,3'-biphenol unit is used and hence an entirely new asymmetry is created, which leads to unsymmetric bisphosphites.

These unsymmetric bisphosphites are thus structurally entirely different from the bisphosphites described in the related art, in which unsymmetric bisphosphite ligands are generated via a particular arrangement of symmetric biaryl units, for example in that the two outer units differ, but the individual units (central unit and outer units) are symmetric per se.

European patent application EP14196179.7 filed Dec. 4, 2014, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A compound having one of the two structures I and II:

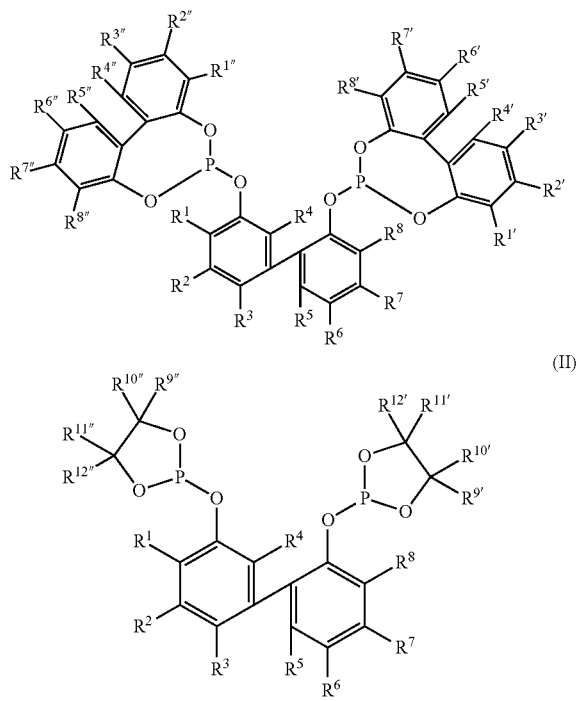

wherein
$R^1$, $R^2$, $R^3$, $R^4$, $R^5$, $R^6$, $R^7$, $R^8$ are each independently selected from the group consisting of:
—H, —$(C_1-C_{12})$-alkyl, —O—$(C_1-C_{12})$-alkyl, —O—$(C_6-C_{20})$-aryl, —$(C_6-C_{20})$-aryl, —S-alkyl, —S-aryl, halogen, COO—$(C_1-C_{12})$-alkyl, CONH—$(C_1-C_{12})$-alkyl, —CO—$(C_1-C_{12})$-alkyl, —CO—$(C_6-C_{20})$-aryl, —COOH, —OH, —$SO_3H$, —CN, —$NH_2$, and —N[$(C_1-C_{12})$-alkyl]$_2$;
$R^{1\prime}$, $R^{2\prime}$, $R^{3\prime}$, $R^{4\prime}$, $R^{5\prime}$, $R^{6\prime}$, $R^{7\prime}$, $R^{8\prime}$, $R^{1\prime\prime}$, $R^{2\prime\prime}$, $R^{3\prime\prime}$, $R^{4\prime\prime}$, $R^{5\prime\prime}$, $R^{6\prime\prime}$, $R^{7\prime\prime}$, $R^{8\prime\prime}$ are each independently selected from the group consisting of:
—H, —$(C_1-C_{12})$-alkyl, —O—$(C_1-C_{12})$-alkyl, —O—$(C_6-C_{20})$-aryl, —$(C_6-C_{20})$-aryl, —S-alkyl, —S-aryl, halogen, COO—$(C_1-C_{12})$-alkyl, CONH—$(C_1-C_{12})$-alkyl, —CO—$(C_1-C_{12})$-alkyl, —CO—$(C_6-C_{20})$-aryl, —COOH, —OH, —$SO_3H$, —$NH_2$, and —N[$(C_1-C_{12})$-alkyl]$_2$;
$R^{9\prime}$, $R^{10\prime}$, $R^{11\prime}$, $R^{12\prime}$, $R^{9\prime\prime}$, $R^{10\prime\prime}$, $R^{11\prime\prime}$, $R^{12\prime\prime}$ are each independently selected from the group consisting of:
—H, and —$(C_6-C_{20})$-aryl;
wherein the alkyl and aryl groups may be substituted.

2. The compound according to claim 1,
wherein $R^1$, $R^2$, $R^3$, $R^4$, $R^5$, $R^6$, $R^7$, $R^8$ are each independently selected from the group consisting of:
—H, —$(C_1-C_{12})$-alkyl, —O—$(C_1-C_{12})$-alkyl, —O—$(C_6-C_{20})$-aryl, —S-alkyl, and —S-aryl.

3. The compound according to claim 1,
wherein $R^1$, $R^2$, $R^3$, $R^4$, $R^5$, $R^6$, $R^7$, $R^8$ are selected from the group consisting of:
—H, —$(C_1-C_{12})$-alkyl, —O—$(C_1-C_2)$-alkyl, and —O—$(C_6-C_{20})$-aryl.

4. The compound according to claim 1,
wherein $R^4$ and $R^5$ are each —H.

5. The compound according to claim 1,
wherein $R^{1\prime}$, $R^{2\prime}$, $R^{3\prime}$, $R^{4\prime}$, $R^{5\prime}$, $R^{6\prime}$, $R^{7\prime}$, $R^{8\prime}$, $R^{1\prime\prime}$, $R^{2\prime\prime}$, $R^{3\prime\prime}$, $R^{4\prime\prime}$, $R^{5\prime\prime}$, $R^{6\prime\prime}$, $R^{7\prime\prime}$, $R^{8\prime\prime}$ are each independently selected from the group consisting of:
—H, —$(C_1-C_{12})$-alkyl, —O—$(C_1-C_{12})$-alkyl, —O—$(C_6-C_{20})$-aryl, —S-alkyl, and —S-aryl.

6. The compound according to claim 1,
wherein $R^{1\prime}$, $R^{2\prime}$, $R^{3\prime}$, $R^{4\prime}$, $R^{5\prime}$, $R^{6\prime}$, $R^{7\prime}$, $R^{8\prime}$, $R^{1\prime\prime}$, $R^{2\prime\prime}$, $R^{3\prime\prime}$, $R^{4\prime\prime}$, $R^{5\prime\prime}$, $R^{6\prime\prime}$, $R^{7\prime\prime}$, $R^{8\prime\prime}$ are each independently selected from the group consisting of:
—H, —$(C_1-C_2)$-alkyl, —O—$(C_1-C_{12})$-alkyl, and —O—$(C_6-C_{20})$-aryl.

7. The compound according to claim 1,
wherein $R^{1\prime}$, $R^{2\prime}$, $R^{3\prime}$, $R^{4\prime}$, $R^{5\prime}$, $R^{6\prime}$, $R^{7\prime}$, $R^{8\prime}$, $R^{1\prime\prime}$, $R^{2\prime\prime}$, $R^{3\prime\prime}$, $R^{4\prime\prime}$, $R^{5\prime\prime}$, $R^{6\prime\prime}$, $R^{7\prime\prime}$, $R^{8\prime\prime}$ are each —H.

8. The compound according to claim 1,
wherein $R^{9\prime}$, $R^{10\prime}$, $R^{11\prime}$, $R^{12\prime}$, $R^{9\prime\prime}$, $R^{10\prime\prime}$, $R^{11\prime\prime}$, $R^{12\prime\prime}$ are each —$(C_6-C_{20})$-aryl.

9. The compound according to claim 1,
wherein $R^{9\prime}$, $R^{10\prime}$, $R^{11\prime}$, $R^{12\prime}$, $R^{9\prime\prime}$, $R^{10\prime\prime}$, $R^{11\prime\prime}$, $R^{12\prime\prime}$ are each phenyl.

10. The compound according to claim 1,
wherein $R^{9\prime}$, $R^{10\prime}$, $R^{11\prime}$, $R^{12\prime}$, $R^{9\prime\prime}$, $R^{10\prime\prime}$, $R^{11\prime\prime}$, $R^{12\prime\prime}$ are each the same radical.

11. The compound according to claim 1,
having the structure (I).

12. The compound according to claim 1,
having the structure (II).

13. A complex, comprising:
a compound according to claim 1; and
a metal atom selected from the group consisting of: Rh, Ru, Co, and Ir.

14. The complex according to claim 13,
wherein said compound has the structure (I).

15. The complex according to claim 13,
wherein said compound has the structure (II).

16. A catalyst for catalyzing a hydroformylation reaction, comprising: the compound according to claim 1.

17. The catalyst according to claim 16,
wherein said compound has the structure (I).

18. The catalyst according to claim 16,
wherein said compound has the structure (II).

19. A process for hydroformylation of an olefin, comprising:
a) initially charging an olefin into a reactor;
b) adding
  i) a complex according to claim 13;
  or
  ii) a compound according to claim 1 and a substance having a metal atom selected from the group consisting of: Rh, Ru, Co, and Ir;
c) feeding into said reactor $H_2$ and CO, to obtain a reaction mixture;
d) heating the reaction mixture, to obtain conversion of the olefin to an aldehyde.

* * * * *